(12) United States Patent
Oviatt, Jr. et al.

(10) Patent No.: US 8,721,870 B2
(45) Date of Patent: May 13, 2014

(54) MEMBRANE SYSTEM WITH SUFFICIENT BUFFERING CAPACITY

(75) Inventors: Henry Oviatt, Jr., Temecula, CA (US); James Petisce, San Clemente, CA (US); Charles Mooney, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 693 days.

(21) Appl. No.: 12/724,583

(22) Filed: Mar. 16, 2010

(65) Prior Publication Data

US 2010/0236923 A1 Sep. 23, 2010

Related U.S. Application Data

(60) Provisional application No. 61/161,671, filed on Mar. 19, 2009.

(51) Int. Cl.
*G01N 27/327* (2006.01)

(52) U.S. Cl.
USPC ............... 205/777.5; 204/403.09; 204/403.1; 204/403.11; 204/403.14

(58) Field of Classification Search
USPC ............... 204/400, 403.09–403.15; 205/775, 205/777.5
See application file for complete search history.

(56) References Cited

U.S. PATENT DOCUMENTS

| | | | |
|---|---|---|---|
| 3,979,274 A * | 9/1976 | Newman ............... | 204/403.09 |
| 4,040,908 A * | 8/1977 | Clark, Jr. ............... | 205/778 |
| 4,525,457 A * | 6/1985 | Sakata et al. ........... | 435/178 |
| 4,970,145 A * | 11/1990 | Bennetto et al. ....... | 204/403.11 |
| 5,118,404 A | 6/1992 | Saito | |
| 5,508,509 A * | 4/1996 | Yafuso et al. .......... | 250/216 |
| 6,740,215 B1 | 5/2004 | Nakaminami et al. | |
| 2002/0068860 A1* | 6/2002 | Clark, Jr. ............... | 600/347 |
| 2004/0065562 A1 | 4/2004 | Hodges | |
| 2007/0202562 A1* | 8/2007 | Curry ..................... | 435/14 |
| 2007/0215465 A1* | 9/2007 | Gu .......................... | 204/403.01 |
| 2008/0200789 A1* | 8/2008 | Brister et al. .......... | 600/347 |
| 2009/0236222 A1* | 9/2009 | Murase et al. ......... | 204/403.14 |

FOREIGN PATENT DOCUMENTS

| | | | | |
|---|---|---|---|---|
| CN | 101151526 A | | 3/2008 | |
| CN | 101360450 A | * | 2/2009 | ........... A61B 5/00 |
| CN | 101151526 B | * | 5/2012 | ........... G01N 27/327 |
| JP | 2001242133 | | 9/2001 | |
| KR | 1020080109478 | | 12/2008 | |

OTHER PUBLICATIONS

Dialog English language translation of CN 101151526 A, application published Mar. 26, 2008.*
Dialog English language translation of CN 101360450 A, application published Feb. 4, 2009.*
International Search Report, Oct. 15, 2010.
Chinese Office Action, Jul. 3, 2013.

* cited by examiner

*Primary Examiner* — Alex Noguerola
(74) *Attorney, Agent, or Firm* — Michael Crapenhoft

(57) ABSTRACT

Electrochemical sensors for measurement of an analyte comprising an analyte sensing membrane comprising at least one salt of acetate ion, carbonate ion, bicarbonate ion, or mixtures thereof. Sensor testing methods comprising contacting an electrochemical sensor with an aqueous solution comprising at least one salt of acetate ion, carbonate ion, bicarbonate ion, or mixtures thereof and contacting the electrochemical sensor with one or more concentrations of analyte, the one or more concentrations of analyte being in the clinical concentration range of the analyte.

22 Claims, 10 Drawing Sheets

MEMBRANE SYSTEM WITH SUFFICIENT BUFFERING CAPACITY

CROSS-REFERENCE TO RELATED APPLICATIONS

The present application claims the benefit of U.S. Provisional Application No. 61/161,671 filed on Mar. 19, 2009, the entire contents thereof being incorporated by reference herein.

TECHNICAL FIELD

The present disclosure relates generally to electrochemical devices for measuring an analyte in a subject. More particularly, the present disclosure relates to devices for measurement of an analyte that incorporates a buffering agent for providing rapid and accurate analyte levels.

BACKGROUND

In addition to the need for rapid and accurate analyte detection is a current need for the sensor technology to perform "out of the box" or otherwise require little or no pre-use testing and or validating. Attempts to provide electrochemical sensors with little or no pre-use testing have been addressed in a number of ways, for example by using software or algorithm-based validation protocols or by incorporating an aqueous reservoir or environment with a known analyte concentration about the sensor. In certain cases, such as an intensive care units (ICUs) setting or for continuous glucose monitoring (CGM) applications, it would be desirable to avoid or eliminate the need to validate or otherwise test the sensor just prior to use. Thus, the current amperometric sensors available on the market may not be capable of "out of the box" performance needed for specific applications, such as ICU monitoring of analyte levels in a subject.

In certain medical applications, patients in ICU or other emergency situations may be often fitted with invasive appliances such as catheters so that vital fluids or medicine may be administered intravenously. A physician determining a fluid dosage to be provided to a patient intravenously may need to know symptoms as quickly as possible that may only be determined through blood tests. Just how quickly the information is needed depends on the gravity of the situation. In some cases, the speed with which a physiological parameter may be determined may be the difference between life and death. In those situations, the requirement of having to pre-test or otherwise validate the sensor just prior to use, just as the practice of drawing a blood sample and sending it off for laboratory analysis, may be entirely unacceptable and/or detrimental to a patient.

A more timely method for measuring blood chemistry to ascertain a physiological parameter of interest may eventually be perfected. Thus, there exists an unmet need to provide intravenous amperometric sensing, in which the concentration of an analyte present in a patient's bloodstream may be determined by locating, within the circulatory system, sensor comprising an electrochemical analyte sensor that has been pre-tested and/or validated in-vitro and produces a rapid and accurate electrical current proportional to the true analyte concentration.

Moreover, pre-testing of electrochemical devices may result in performance that is not commensurate with actual end-use, and as a result, potentially viable sensor constructs may be erroneously dismissed. It is generally known that when testing an electrochemical analyte sensor in vitro, the testing solution is buffered to simulate the pH of the actual end-use environment of the sensor. Typically the buffer solution is PBS and the pH is adjusted to that of physiological fluids found in the test subject (e.g., blood, interstitial fluids, urine, etc.). It is also generally observed in sensor development and/or quality assurance (QC) testing of electrochemical analyte sensors that the output signal may drift over a period of time at a given (and relatively constant) analyte concentration range. When such a drift is observed, it is typically regarded as an indication that the sensor construct and any of its components is not optimized and/or otherwise inadequate and may result in re-design or QC rejection of the sensor and possibly all of the sensors fabricated together therewith.

Thus, a testing method for electrochemical analyte sensors that otherwise provides performance that is commensurate with actual end-use and/or adequately buffers the microenvironment of an enzyme within a multi-layer analyte sensing membrane, is desirable.

SUMMARY

In a first embodiment, an electrochemical analyte sensor is provided comprising at least one electrode having an electroactive surface; an analyte sensing membrane, at least a portion of the membrane covering the electroactive surface, the membrane comprising: an optional interference layer; an enzyme layer; optionally a hydrophilic polymer layer; and at least one buffering agent associated with the analyte sensing membrane. The optional hydrophilic polymer layer is positioned (i) between the electroactive surface and the interference layer and/or (ii) between the interference layer and the enzyme layer. The buffering agent comprises at least one salt of acetate ion, carbonate ion, bicarbonate ion, or combinations thereof.

In one aspect of the first embodiment, the buffering agent comprises carbonate ion, bicarbonate ion, or combinations thereof.

In another aspect of the first embodiment, the buffering agent comprises a polyelectrolyte where the anion of the polyelectrolyte is acetate, bicarbonate, carbonate, or mixtures of the anions.

In another aspect of the first embodiment, the buffering agent is present in an amount sufficient to neutralize acidic, electrochemically produced by-products of the analyte sensing membrane over the pharmacological concentration range of analyte when tested in vivo.

In another aspect of the first embodiment, the sensor comprises at least one salt comprising acetate ion, carbonate ion, bicarbonate ion, or mixtures thereof, the at least one salt being: (i) deposited as a dried layer between the electroactive surface and the interference layer; (ii) deposited as a dried layer between the interference layer and the enzyme layer; (iii) associated with the hydrophilic polymer layer, the hydrophilic layer positioned (a) between the electrode surface and the interference layer and/or (b) between the interference layer and the enzyme layer; (iv) associated with the enzyme layer; or (v) any or all combinations of (i)-(iv). The analyte sensing membrane further comprises a flux-limiting layer, the flux-limiting layer encapsulating the membrane eliminating and/or reducing diffusion of the buffering agent from the analyte sensing membrane during use.

In a second embodiment, an electrochemical analyte sensor is provided. The sensor comprises at least one working electrode having an electroactive surface; an analyte sensing membrane, an optional interference layer, an enzyme layer, at least one salt, and a flux-limiting layer. The analyte sensing layer may comprise an optional hydrophilic layer positioned (i) between the electroactive surface and the optional interference layer and/or (ii) between the optional interference layer and the enzyme layer, the hydrophilic layer comprising at least one hydrophilic polymer and excluding an enzyme. The optional interference layer comprises a cellulosic derivative. The at least one salt comprises acetate ion, carbonate ion, bicarbonate ion, or mixtures thereof. The at least one salt is: (i) deposited as a dried layer between the electroactive surface and the interference layer; (ii) deposited as a dried layer between the optional interference layer and the enzyme layer; (iii) associated with the hydrophilic polymer layer, the hydrophilic layer positioned (a) between the electrode surface and the optional interference layer and/or (b) between the optional interference layer and the enzyme layer; (iv) associated with the enzyme layer; or (v) any or all combinations of (i)-(iv). The flux-limiting layer covers the enzyme layer, the interference layer, the optional hydrophilic layer, and the at least one electrode.

In a third embodiment, a method of testing an electrochemical analyte sensor is provided. The method comprises providing an electrochemical sensor, contacting the electrochemical sensor to an aqueous solution of a buffering agent, the buffering agent providing a signal drift at a concentration of glucose of 400 mg/dL or more of 10% or less over 1 hour or more, contacting the electrochemical sensor to one or more concentrations of analyte in the clinical concentration range of the analyte, and testing the electrochemical analyte sensor.

In one aspect of the third embodiment, the buffering agent is present in an amount sufficient to (i) neutralize acidic, electrochemically generated by-products of the electrochemical analyte sensor over the clinical concentration range of the analyte in vitro; and/or (ii) provide essentially a constant output current at the upper end of the clinical concentration range of the analyte for at least two hours when tested in vitro.

In another aspect of the third embodiment, the buffering agent comprises carbonate ion, bicarbonate ion, or a mixture of carbonate and bicarbonate ions.

In another aspect of the third embodiment, the buffering agent provides a signal drift at a concentration of glucose of 400 mg/dL or more of 10% or less over 2 hours or more.

In another aspect of the third embodiment, the signal drift at a concentration of glucose of 400 mg/dL or more of 10% or less is maintained for at time of greater than 8 hr.

This invention is also applicable to glucose test solutions and glucose calibration solutions. Specifically, these solutions will be formulated to have sufficient capacity to buffer acidic buildup of enzymatic by-products, such as gluconic acid, around the microenvironment of the enzyme of a glucose sensor. Consequently, the glucose sensor immersed into a solution of this invention disclosure will be enabled to provide an output signal which is 1) stable as a function of solution immersion time and 2) linear as a function of glucose concentration.

DETAILED DESCRIPTION

Figure 1:
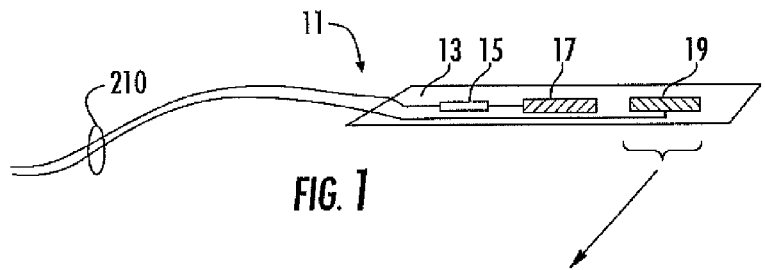
FIG. 1 shows an amperometric sensor in the form of a flex circuit having a working electrode coated with a flux-limiting membrane according to an embodiment of the invention.

In general, electrochemical analyte sensors and in-vitro testing methods are disclosed that provide rapid chemical, electrical and physical equilibrium with their environment and as a result, provide fast and accurate analyte levels. More particularly, the present disclosure relates to devices for measurement of an analyte that incorporates a buffering agent for providing rapid and accurate analyte levels, and/or an in-vitro testing method to pre-test and to validate the device. Such sensors and method of in-vitro testing are of particular use in more demanding sensing applications, such as ICU monitoring. Applicants have surprisingly observed that a specific type of buffering agent associated with the analyte sensing membrane architecture of an electrochemical sensor, or in a testing solution for the sensor, substantially maintains signal output of the sensor corresponding to the concentration of analyte. The signal output is maintained more than that of comparatively buffered solutions or comparative sensor architectures substantially without the specific buffering agent. In addition, the Applicants have surprisingly observed that the use of specific buffering agents, for example, buffering agents comprising acetate ion, bicarbonate ion, carbonate ion, and mixtures thereof substantially eliminate or reduce the development time, validation, and QC-related testing needed for commercialization of electrochemical sensors.

While not to be held to any particular theory, Applicants generally believe that the buffering agent selected from at least one salt of acetate ion, bicarbonate ion, carbonate ion, or mixtures thereof, reduces or eliminates changes in local pH within the analyte sensing membrane microenvironment. For example, changes in local pH within the analyte sensing membrane microenvironment resulting from the generation of gluconic acid from the reaction of glucose with glucose oxidase. Thus, the buffering agent disclosed herein maintains the sensitivity of the enzyme within the analyte sensing membrane microenvironment, which in turn provides for an improved or otherwise stable signal output during periods of relatively constant analyte concentration, and particularly, relatively high concentrations of analyte, and even more particularly, relatively high concentrations of analyte that are maintained for extended periods of time. Constant analyte concentration conditions may be present or provided during development of the sensor, during validation, or QC-related testing of the sensor, or during in vivo use of the sensor.

The following description and examples illustrate some exemplary embodiments of the disclosed invention in detail. Those of skill in the art will recognize that there may be numerous variations and modifications of this invention that may be encompassed by its scope. Accordingly, the description of a certain exemplary embodiment is not intended to limit the scope of the present invention.

Definitions

In order to facilitate an understanding of the various aspects of the invention, the following are defined below.

The term "analyte" as used herein refers without limitation to a substance or chemical constituent of interest in a biological fluid (for example, blood) that may be analyzed. The analyte may be naturally present in the biological fluid, the analyte may be introduced into the body, or the analyte may be a metabolic product of a substance of interest or an enzymatically produced chemical reactant or chemical product of a substance of interest. Preferably, analytes include chemical entities capable of reacting with at least one enzyme and quantitatively yielding an electrochemically reactive product that is either amperiometrically or voltammetrically detectable.

The phrases and terms "analyte measuring device," "sensor," and "sensor assembly" as used herein refer without limitation to an area of an analyte-monitoring device that enables the detection of at least one analyte. For example, the sensor may comprise a non-conductive portion, at least one working electrode, a reference electrode, and a counter electrode (optional), forming an electrochemically reactive surface at one location on the non-conductive portion and an electronic connection at another location on the non-conductive portion, and a one or more layers over the electrochemically reactive surface.

The term "break-in" as used herein refers without limitation to a time duration, after sensor deployment, where an electrical output from the sensor achieves a substantially constant value following contact of the sensor with a solution. Break-in is inclusive of configuring the sensor electronics by applying different voltage settings, starting with a higher voltage setting and then reducing the voltage setting and/or pre-treating the operating electrode with a negative electric current at a constant current density. Break-in is inclusive of chemical/electrical equilibrium of one or more of the sensor components such as membranes, layers, enzymes and electronics, and may occur prior to calibration of the sensor output. For example, following a potential input to the sensor, an immediate break-in would be a substantially constant current output from the sensor. By way of example, an immediate break-in for a glucose electrochemical sensor after contact with a solution, would be a current output representative of +/−5 mg/dL of a calibrated glucose concentration within about thirty minutes or less after deployment. The term "break-in" is well documented and is appreciated by one skilled in the art of electrochemical glucose sensors, however it may be exemplified for a glucose sensor, as the time at which reference glucose data (e.g., from an SMBG meter) is within +/−5 mg/dL of the measured glucose sensor data.

The phrase "buffering agent" as used herein generally refers to agents that are or become the main components of a buffer solution. For example, the "buffering agent," when contacted by an aqueous solution comprising an analyte, modifies and/or maintains the pH of the solution, where the pH of the solution may be the same or different than that prior to contact of the solution with the buffering agent. In one specific example, the buffering agent forms an active agent of a buffer solution associated with an analyte sensing membrane upon contact with an aqueous medium comprising or presented with the analyte. In a preferred aspect, the buffering agent forms an active agent of a buffer solution associated with a glucose oxidase comprising sensing membrane upon contact with an aqueous medium comprising or presented with glucose. In another specific example, the buffering agent forms an active agent of a buffer solution associated with an aqueous medium comprising an analyte used for testing an electrochemical sensor responsive to the analyte. In a preferred aspect, the buffering agent forms an active agent of a buffer solution associated with an aqueous medium comprising glucose used for testing an electrochemical glucose sensor. In a more preferred aspect, the buffering agent comprises at least one of acetate ion, bicarbonate ion, carbonate ion, or mixtures thereof, or comprises about 10× phosphate buffered saline (10×PBS), or comprises phosphate buffered saline (PBS) in combination with one of acetate ion, bicarbonate ion, carbonate ion. In an even more preferred aspect, the buffering agent comprises at least one of acetate ion, bicarbonate ion, carbonate ion, or mixtures thereof within the (micro)environment of the enzyme of the analyte sensing membrane. In a preferred aspect, the buffering agent is an aqueous soluble salt of ammonium, alkyl ammonium, alkali, alkali earth, or polycation, the salt comprising at least one of acetate ion, bicarbonate ion, carbonate ion, or mixtures thereof.

The phrase "capable of" as used herein, when referring to recitation of function associated with a recited structure, is inclusive of all conditions where the recited structure can actually perform the recited function. For example, the phrase "capable of" includes performance of the function under normal operating conditions, experimental conditions or laboratory conditions, as well as conditions that may not or can not occur during normal operation.

The term "cellulose acetate butyrate" as used herein refers without limitation to compounds obtained by contacting cellulose with acetic anhydride and butyric anhydride.

The term "comprising" and its grammatical equivalents, as used herein is synonymous with "including," "containing," or "characterized by," and is inclusive or open-ended and does not exclude additional, un-recited elements or method steps.

The phrases "continuous analyte sensing" and "continual analyte sensing" (and the grammatical equivalents "continuously" and continually") as used herein refer without limitation to a period of analyte concentration monitoring that is continuously, continually, and/or intermittently (but regularly) performed.

The phrase "continuous glucose sensing" as used herein refers without limitation to a period of glucose concentration monitoring that is continuously, continually, and/or intermittently (but regularly) performed. The period may, for example, at time intervals ranging from fractions of a second up to, for example, 1, 2, or 5 minutes, or longer.

The term "cover" and its grammatical equivalents is used herein refers without limitation to its normal dictionary definition, and is inclusive of one or more intervening layers. For example, a layer "covering" at least a portion of an electroactive surface is inclusive of one or more intervening layers between the layer and the electroactive surface.

The terms "crosslink" and "crosslinking" as used herein refer without limitation to joining (e.g., adjacent chains of a polymer and/or protein) by creating covalent or ionic bonds. Crosslinking may be accomplished by known techniques, for example, thermal reaction, chemical reaction or ionizing radiation (for example, electron beam radiation, UV radiation, X-ray, or gamma radiation). For example, reaction of a dialdehyde such as glutaraldehyde with a hydrophilic polymer enzyme composition would result in chemical crosslinking of one or more of the enzyme and/or hydrophilic polymer.

The phrase "electroactive surface" as used herein is refers without limitation to a surface of an electrode where an electrochemical reaction takes place. For example, at a predetermined potential, $H_2O_2$ reacts with the electroactive surface of a working electrode to produce two protons ($2H^+$), two electrons ($2e^-$) and one molecule of oxygen ($O_2$), for which the electrons produce a detectable electronic current. The electroactive surface may include on at least a portion thereof, a chemically or covalently bonded adhesion promoting agent, such as aminoalkylsilane, and the like.

The phrase "enzyme layer" as used herein refers without limitation to a permeable or semi-permeable membrane comprising one or more domains that may be permeable to reactants and/or co-reactants employed in determining the analyte of interest. As an example, an enzyme layer comprises an glucose oxidase enzyme and a hydrophilic polymer, the enzyme catalyzing an electrochemical reaction with glucose and oxygen to permit measurement of a concentration of glucose. The enzyme layer may further include at least one protein, or a natural or synthetic material. In a preferred aspect, the enzyme layer intentionally excludes protein from an animal source having a known or suspected pathological, viral, or immunological effect on humans, for example, any bovine protein, and especially bovine protein associated with Bovine Spongiform Encephalopathy (BSE), to avoid the possibility of inadvertent infection of the host. In another aspect, the enzyme layer intentionally excludes redox-mediators, especially redox-mediators having transition metals associated therewith in view of their known toxicity. The exclusion of redox-mediators is driven at least in part by the possibilty of release of toxic metals in to the host during use.

The term "flux-limiting membrane" as used herein refers to a semi-permeable membrane that controls the flux of oxygen and other analytes to the underlying enzyme layer. By way of example, for a glucose sensor, the flux-limiting membrane preferably renders oxygen in a non-rate-limiting excess. As a result, the upper limit of linearity of glucose measurement is extended to a much higher value than that which is achieved without the flux-limiting membrane.

The terms "interferants," "interferents" and "interfering species," as used herein refer without limitation to effects and/or species that otherwise interfere with a measurement of an analyte of interest in a sensor to produce a signal that does not accurately represent the analyte measurement. For example, in an electrochemical sensor, interfering species may be compounds with oxidation potentials that substantially overlap the oxidation potential of the analyte to be measured.

The term "polyelectrolyte" as used herein refers to a high molecular weight material having pendent ionizable groups. The molecular weight of polyelectrolytes may range from at least about a thousand to at least about a million Daltons. In one aspect, polyelectrolytes are exclusive of polymers with terminal ionizable groups and essentially no pendent ionizable groups, for example, Nafion.

The term "subject" as used herein refers without limitation to mammals, particularly humans and domesticated animals.

The phrase "vinyl ester monomeric units" as used herein refers to compounds and compositions of matter which are formed from the polymerization of an unsaturated monomer having ester functionality. For example, polyethylene vinyl acetate polymer and copolymers thereof are compounds comprising vinyl ester monomeric units.

Sensor System and Sensor Assembly

The aspects of the invention herein disclosed relate to the use of an analyte sensor system that measures a concentration of analyte of interest or a substance indicative of the concentration or presence of the analyte. The sensor system is a continuous device, and may be used, for example, as or part of a subcutaneous, transdermal (e.g., transcutaneous), or intravascular device. The analyte sensor may use an enzymatic, chemical, electrochemical, or combination of such methods for analyte-sensing. The output signal is typically a raw signal that is used to provide a useful value of the analyte of interest to a user, such as a patient or physician, who may be using the device. Accordingly, appropriate smoothing, calibration, and evaluation methods may be applied to the raw signal.

Generally, the sensor comprises at least a portion of the exposed electroactive surface of a working electrode surrounded by a plurality of layers. Preferably, an interference layer is deposited over and in contact with at least a portion of the electroactive surfaces of the sensor (working electrode and optionally the reference electrode) to provide protection of the exposed electrode surface from the biological environment and/or limit or block of interferents. An enzyme layer is deposited over and in contact with at least a portion of the interference layer. In one aspect, the interference layer and enzyme layer provides for rapid response and stabilization of the signal output of the sensor and/or eliminates the need to pre-treat the electroactive surface of the electrode with fugitive species, such as salts and electrolyte layers or domains, which simplifies manufacture and reduces lot-to-lot variability of the disclosed sensors.

One exemplary embodiment described in detail below utilizes a medical device, such as a catheter, with a glucose sensor assembly. In one aspect, a medical device with an analyte sensor assembly is provided for inserting the into a subject's vascular system. The medical device with the analyte sensor assembly may include associated therewith an electronics unit associated with the sensor, and a receiver for receiving and/or processing sensor data. Although a few exemplary embodiments of continuous glucose sensors may be illustrated and described herein, it should be understood that the disclosed embodiments may be applicable to any device capable of substantially continual or substantially continuous measurement of a concentration of analyte of interest and for providing an rapid and accurate output signal that is representative of the concentration of that analyte.

Electrode and Electroactive Surface

The electrode and/or the electroactive surface of the sensor or sensor assembly disclosed herein comprises a conductive material, such as platinum, platinum-iridium, palladium, graphite, gold, carbon, conductive polymer, alloys, ink or the like. Although the electrodes can by formed by a variety of manufacturing techniques (bulk metal processing, deposition of metal onto a substrate, or the like), it may be advantageous to form the electrodes from screen printing techniques using conductive and/or catalyzed inks. The conductive inks may be catalyzed with noble metals such as platinum and/or palladium.

In one aspect, the electrodes and/or the electroactive surfaces of the sensor or sensor assembly are formed on a flexible substrate, such as a flex circuit. In one aspect, a flex circuit is part of the sensor and comprises a substrate, conductive traces, and electrodes. The traces and electrodes may be masked and imaged onto the substrate, for example, using screen printing or ink deposition techniques. The trace and the electrodes, and the electroactive surface of the electrode may be comprised of a conductive material, such as platinum, platinum-iridium, palladium, graphite, gold, carbon, conductive polymer, alloys, ink or the like.

In one aspect, a counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction: Glucose+$O_2$→Gluconate+$H_2O_2$. Oxidation of $H_2O_2$ by the working electrode is balanced by reduction of any oxygen present, or other reducible species at the counter electrode. The $H_2O_2$ produced from the glucose oxidase reaction reacts at the surface of working electrode and produces two protons ($2H^+$), two electrons ($2e^-$), and one oxygen molecule ($O_2$).

In one aspect, additional electrodes may be included within the sensor or sensor assembly, for example, a three-electrode system (working, reference, and counter electrodes) and/or one or more additional working electrodes configured as a baseline subtracting electrode, or which is configured for measuring additional analytes. The two working electrodes may be positioned in close proximity to each other, and in close proximity to the reference electrode. For example, a multiple electrode system may be configured wherein a first working electrode is configured to measure a first signal comprising glucose and baseline and an additional working electrode substantially similar to the first working electrode without an enzyme disposed thereon is configured to measure a baseline signal consisting of baseline only. In this way, the baseline signal generated by the additional electrode may be subtracted from the signal of the first working electrode to produce a glucose-only signal substantially free of baseline fluctuations and/or electrochemically active interfering species.

In one aspect, the sensor comprises from 2 to 4 electrodes. The electrodes may include, for example, the counter electrode (CE), working electrode (WE1), reference electrode (RE) and optionally a second working electrode (WE2). In one aspect, the sensor will have at least a CE and WE1. In one aspect, the addition of a WE2 is used, which may further improve the accuracy of the sensor measurement. In one aspect, the addition of a second counter electrode (CE2) may be used, which may further improve the accuracy of the sensor measurement.

The electroactive surface may be treated prior to application of any of the subsequent layers. Surface treatments may include for example, chemical, plasma or laser treatment of at least a portion of the electroactive surface. By way of example, the electrodes may be chemically or covalently contacted with one or more adhesion promoting agents. Adhesion promoting agents may include for example, aminoalkylalkoxylsilanes, epoxyalkylalkoxylsilanes and the like. For examples, one or more of the electrodes may be chemically or covalently contacted with a solution containing 3-glycidoxypropyltrimethoxysilane.

In some alternative embodiments, the exposed surface area of the working (and/or other) electrode may be increased by altering the cross-section of the electrode itself. Increasing the surface area of the working electrode may be advantageous in providing an increased signal responsive to the analyte concentration, which in turn may be helpful in improving the signal-to-noise ratio, for example. The cross-section of the working electrode may be defined by any regular or irregular, circular or non-circular configuration.

Buffering Agent

In one aspect, the buffering agent comprises at least one of acetate ion, carbonate ion, bicarbonate ion, and mixtures thereof. In another aspect, the buffering agent comprises an aqueous solution of phosphate buffered saline (PBS) of at least 0.030 molality $Na_2HPO_4$ and at least 0.006 molality $KH_2PO_4$, or any combination of acetate ion, carbonate ion, bicarbonate ion, and phosphate buffered saline (PBS). When present in aqueous media, the buffering agent is capable of providing acetate ion, carbonate ion, bicarbonate ion and mixtures thereof. In a preferred aspect, the buffering agent forms an active agent of a buffer solution associated with the analyte sensing membrane or an aqueous medium comprising glucose used for testing an electrochemical glucose sensor. The buffering agent is present in an amount sufficient to neutralize acidic, electrochemically produced by-products of the electrochemical analyte sensor over the clinical concentration range of analyte when used in vivo or in vitro. In a more preferred aspect, the buffering agent comprises at least one of acetate ion, bicarbonate ion, carbonate ion, 3× or greater PBS, or mixtures thereof. In an even more preferred aspect, the buffering agent comprises at least one of acetate ion, bicarbonate ion, carbonate ion, 10×PBS or mixtures thereof within the (micro)environment of the enzyme of the analyte sensing membrane. In a preferred aspect, the buffering agent is a salt of ammonium, alkylammonium, alkali, alkali earth, or polycation, the salt comprising at least one of acetate ion, bicarbonate ion, carbonate ion, or mixtures thereof. In a more preferred aspect, the buffering agent comprises the sodium, potassium, ammonium, or polycation salt of acetate, carbonate or bicarbonate, or mixtures thereof.

In one aspect, the buffering agent is a polyelectrolyte comprising acetate ion, carbonate ion, bicarbonate ion, or mixtures thereof. Polyelectrolytes are high molecular weight materials having pendent ionizable groups. As electrolytes, polyelectrolytes exhibit the advantageous ionic properties required for stable sensor functioning, such as charge neutralization and charge transfer abilities. Due to their large size, polyelectrolytes substantially reduce or eliminate diffusion of the electrolytic (fugitive) species through the analyte sensing membrane, for example the acetate ion, carbonate ion, or bicarbonate ion. Thus, a polyelectrolyte comprising acetate, carbonate, bicarbonate and mixtures thereof is believed to substantially maintain electroneutrality while providing a non-fugitive buffering system for the analyte sensing membrane. Generally, polyelectrolytes have numerous ionizable groups, and thus may be highly charged. In one aspect, the polyelectrolyte may be comprised of multiple ionizable groups. In a further aspect, the polyelectrolyte preferably is without terminal ionizable groups, for example, Nafion-based polyelectrolytes. Preferred polyelectrolytes are cationic polyelectrolyte salts, or polycations (polymers containing repeat linkages with positive charges) comprising acetate ion, carbonate ion, bicarbonate ion or mixtures thereof.

Preferred aspects of the invention utilize a polyelectrolyte comprising pharmaceutically acceptable polycations comprising acetate, carbonate, bicarbonate and mixtures thereof. A pharmaceutically acceptable salt is one which is safe and effective for use in humans. Examples of polycations or polycation precursors include, for example, linear or branched poly(ethylene imine), poly(allylamine), polyalkylenepolyamine, poly (diallyldimethylammonium), poly(acrylic acid), poly(methacrylic acid), poly(styrene sulfonate), poly (2-acrylamido-2-methyl-1-propane-sulfonic acid), (3-acrylamidopropyetrismethylammonium), N-(3-aminopropyl) methacrylamide, poly-4-vinylpyridine, polyacrylonitrile, polylysine, polyornithine, polyhistidine, polyarginine, polytryptophan, poly-2,4-diaminobutyric acid, polylysine, polyornithine, polyhistidine, polyarginine, polytryptophan, poly-2,4-diaminobutyric acid, poly-2,3-diaminopropionic acid, protamine, and polypeptide having at least one or more kinds of amino acid residues in a polypeptide chain selected from the group consisting of lysine, histidine, arginine, tryptophan, ornithine, 2,4-diaminobutyric acid and 2,3-diaminopropionic acid, dimethylamine-epichlorohydrin condensation products, polyamine type compounds include condensation products of polyalkylenepolyamine and guanidine derivative, polyamidopolyamines, and mixtures thereof. One skilled in the art of polymer science can appreciate the very wide diversity of possible polycations and combinations thereof and the associated counterions of acetate, carbonate, bicarbonate and mixtures thereof, and will recognize that the list above is not by any means exhaustive, and other possible combinations are considered to be inclusive, including the possible combination of one or more polycations. The polycation salt comprising acetate, carbonate, bicarbonate, or mixtures thereof may be prepared by direct reaction of the free acid of the polycation with the conjugate base of the acetate, carbonate or bicarbonate, or by ion exchange methods of polycation of other anions, using methods generally known in the art.

In one aspect, the buffering agent comprising acetate ion, carbonate ion, bicarbonate ion, or mixtures thereof are present in a molar concentration in excess of any other buffering agent. For example, the buffering agent is present in a molar (or molal) excess to that of the principle components of phosphate buffered saline (PBS) buffer, where a 1×PBS buffer solution would typically have a concentration of 137 mM NaCl, 10 mM Phosphate, 2.7 mM KCl, and a pH of 7.4, the phosphates being the principle buffer components. In a preferred aspect, the concentration of buffering agent is between 10 mM and 200 mM, more preferably between 20 mM and about 150 mM, and most preferably, between 25 mM and 60 mM. Greater amounts of buffering agent may be used. In other aspects, the buffering agent is used together with PBS, provided that the amount of non-PBS buffering agent is at least 20 mM. For example, it has been found that a buffering agent comprising carbonate ion at a concentration of about 20 mM provides superior signal output performance at high levels of analyte for extended periods of time compared with 1×PBS, and even 10×PBS buffered solutions, at pH about 7.4. In another aspect, the buffering agent is present in an aqueous solution for testing of a sensor such that the aqueous solution comprises acetate ion, carbonate ion, bicarbonate ion, phosphate buffered saline (PBS) of at least 0.030 molality $Na_2HPO_4$ and 0.006 molality $KH_2PO_4$, or any combination of acetate ion, carbonate ion, bicarbonate ion, and phosphate buffered saline (PBS). For example, the aqueous solution may contain 20 mM bicarbonate and 1×PBS or may contain only PBS at least 0.030 molality $Na_2HPO_4$ and 0.006 molality $KH_2PO_4$.

In one preferred aspect, the buffering agent is: (i) deposited as a dried layer between the electroactive surface and the interference layer; (ii) deposited as a dried layer between the interference layer and the enzyme layer; (iii) associated with the optional hydrophilic polymer layer, the hydrophilic layer positioned (a) between the electroactive surface and the interference layer and/or (b) between the interference layer and the enzyme layer; (iv) associated with the enzyme layer; or (v) any or all combinations of (i)-(iv).

Optional Hydrophilic Layer

In one aspect, the analyte sensing membrane of the electrochemical sensor optionally comprises a hydrophilic layer. The hydrophilic layer may be positioned over the electrode/electroactive surface and/or in direct contact with the electrode/electroactive surface. Likewise, the hydrophilic layer may be positioned over/under another layer of the analyte sensing membrane, such as an interference layer and/or an enzyme layer. The hydrophilic layer may be selected from a poly-N-vinylpyrrolidone (PVP), poly-N-vinyl-3-ethyl-2-pyrrolidone, poly-N-vinyl-4,5-dimethyl-2-pyrrolidone, polyacrylamide, poly-N,N-dimethylacrylamide, polyvinyl alcohol, polymers with pendent ionizable groups, and copolymers or blends thereof. Preferably, the hydrophilic layer comprises poly-N-vinylpyrrolidone or polyelectrolytes. The hydrophilic layer may comprise the buffering agent.

Optional Interference Layer

In one aspect, the analyte sensing membrane of the electrochemical sensor optionally comprises an interferent layer to eliminate or reduce the contact of interferents with the working electrode. Interferents may be molecules or other species that may be reduced or oxidized at the electrochemically reactive surfaces of the sensor, either directly or via an electron transfer agent, to produce a false positive analyte signal (e.g., a non-analyte-related signal). This false positive signal generally causes the subject's analyte concentration to appear higher than the true analyte concentration. For example, in a hypoglycemic situation, where the subject has ingested an interferent (e.g., acetaminophen), the artificially high glucose signal may lead the subject or health care provider to believe that they are euglycemic or, in some cases, hyperglycemic. As a result, the subject or health care provider may make inappropriate or incorrect treatment decisions.

Any material suitable for use as an interference layer may be used in accordance with the sensors and methods herein disclosed. In one aspect, an interference layer is provided on the sensor or sensor assembly that substantially restricts or eliminates the passage there through of one or more interfering species. Suitable interference materials include, for example, celluloses and their derivatives, polyurethanes such as silicone- and/or carbonate-containing polyurethane elastomers, Nafion, polyanionic resins, polycarbonates, polysulfones, and the like.

Interfering species for a glucose sensor include, for example, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, urea and uric acid. The interference layer may be less permeable to one or more of the interfering species than to a target analyte species. The interference layer may be perforated to have openings of a particular size that restricts the permeability of one or more of the interfering species but allows the target analyte species to pass, for example. In one aspect, the interferent layer comprises the buffering agent comprising at least one salt of acetate ion, carbonate ion, bicarbonate ion, or mixtures thereof. In another aspect, a dried layer of buffering agent comprising at least one salt of acetate ion, carbonate ion, bicarbonate ion, or mixtures thereof is positioned (i) between the interferent layer and the electrode surface and/or (ii) over the interference layer. In an embodiment, the interference layer is formed from one or more cellulosic derivatives. Cellulose derivatives include cellulose acetate, cellulose butyrate, cellulose phthalate, cellulose propionate, cellulose trimellitate, and the like. In one aspect, mixed ester cellulosic derivatives may be used, for example, cellulose acetate butyrate, cellulose acetate phthalate, cellulose acetate propionate, cellulose acetate trimellitate, as well as their copolymers and terpolymers, with other cellulosic or non-cellulosic monomers, including cross-linked variations of the above. Other polymers, such as polymeric polysaccharides having similar properties to cellulosic derivatives, may be used as an interference material or in combination with the above cellulosic derivatives.

Other esters of cellulose may be blended with the mixed ester cellulosic derivatives, for example, cellulose acetate blended with cellulose acetate butyrate. Discrete layers of different cellulosic derivatives as described above may make up the interference layer.

In one aspect, the interference layer is formed from cellulose acetate butyrate. Cellulose acetate butyrate is a cellulosic polymer having both acetyl and butyl groups, and hydroxyl groups. A cellulose acetate butyrate having about 35% or less acetyl groups, about 10% to about 25% butyryl groups, and hydroxyl groups making up the remainder may be used. A cellulose acetate butyrate having from about 25% to about 34% acetyl groups and from about 15 to about 20% butyryl groups may also be used, however, other amounts of acetyl and butyryl groups may be used. A preferred cellulose acetate butyrate contains from about 28% to about 30% acetyl groups and from about 16 to about 18% butyryl groups.

Cellulose acetate butyrate with a molecular weight of about 10,000 daltons to about 75,000 daltons is preferred, preferably from about 15,000, 20,000, or 25,000 daltons to about 50,000, 55,000, 60,000, 65,000, or 70,000 daltons, and more preferably about 65,000 daltons is employed. In certain embodiments, however, higher or lower molecular weights may be used or a blend of two or more cellulose acetate butyrates having different molecular weights may be used.

A plurality of layers of cellulose acetate butyrate may be combined to form the interference layer in some embodiments, for example, two or more layers may be employed. It may be desirable to employ a mixture of cellulose acetate butyrates with different molecular weights in a single solution, or to deposit multiple layers of cellulose acetate butyrate from different solutions comprising cellulose acetate butyrate of different molecular weights, different concentrations, and/ or different chemistries (e.g., wt functional groups). Additional substances in the casting solutions or dispersions may be used, e.g., casting aids, defoamers, surface tension modifiers, functionalizing agents, crosslinking agents, other polymeric substances, substances capable of modifying the hydrophilicity/hydrophobicity of the resulting layer, and the like.

The interference material may be sprayed, cast, coated, or dipped directly to the electroactive surface(s) of the sensor to provide the interference layer. The dispensing of the interference material may be performed using any known thin film technique. Two, three or more layers of interference material may be formed by the sequential application and curing and/ or drying of the casting solution.

The concentration of solids in the casting solution may be adjusted to deposit a sufficient amount of solids or film on the electrode in one layer (e.g., in one dip or spray) to form a layer sufficient to block an interferant with an oxidation or reduction potential otherwise overlapping that of a measured species (e.g., $H_2O_2$), measured by the sensor. For example, the casting solution's percentage of solids may be adjusted such that only a single layer is required to deposit a sufficient amount to form a functional interference layer that substantially prevents or reduces the equivalent glucose signal of the interferant measured by the sensor. A sufficient amount of interference material would be an amount that substantially prevents or reduces the equivalent glucose signal of the interferant of less than about 30, 20 or 10 mg/dl. By way of example, the interference layer is preferably configured to substantially block about 30 mg/dl of an equivalent glucose signal response that otherwise would be produced by acetaminophen by a sensor without an interference layer. Such equivalent glucose signal response produced by acetaminophen would include a therapeutic dose of acetaminophen. Any number of coatings or layers formed in any order may be suitable for forming the interference layer of the embodiments disclosed herein.

In one aspect, the interference layer is deposited either directly onto the electroactive surfaces of the sensor or onto a material or layer in direct contact with the surface of the electrode. Preferably, the interference layer is deposited directly onto the electroactive surfaces of the sensor substantially without an intervening material or layer in direct contact with the surface of the electrode. It has been surprisingly found that configurations comprising the interference layer deposited directly onto the electroactive surface of the sensor substantially eliminates the need for an intervening layer between the electroactive surface and the interference layer while still providing a rapid and accurate signal representative of the analyte.

The interference layer may be applied to provide a thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes may also be desirable in certain embodiments, but thinner membranes may be generally preferred because they generally have a lower affect on the rate of diffusion of hydrogen peroxide from the enzyme membrane to the electrodes.

Enzyme Layer

The sensor or sensor assembly disclosed herein includes an enzyme layer. The enzyme layer may comprise a hydrophilic polymer. In one aspect, the enzyme layer comprises an enzyme deposited directly onto at least a portion of the interference layer. In one aspect, the enzyme layer comprises the buffering agent comprising at least one salt of acetate ion, carbonate ion, bicarbonate ion, or mixtures thereof.

In one aspect, the enzyme layer comprises a enzyme and a hydrophilic polymer selected from poly-N-vinylpyrrolidone (PVP), poly-N-vinyl-3-ethyl-2-pyrrolidone, poly-N-vinyl-4, 5-dimethyl-2-pyrrolidone, polyacrylamide, poly-N,N-dimethylacrylamide, polyvinyl alcohol, polymers with pendent ionizable groups, polyurethanes and copolymers thereof. Preferably, the enzyme layer comprises poly-N-vinylpyrrolidone. The enzyme layer may be substantially free of additional components, such as cross-linking agents and other proteins. Most preferably, the enzyme layer comprises glucose oxidase, poly-N-vinylpyrrolidone and an amount of crosslinking agent sufficient to immobilize the enzyme.

The molecular weight of the hydrophilic polymer of the enzyme layer is such that fugitive species are prevented or substantially inhibited from leaving the sensor environment and more particularly, fugitive species are prevented or substantially inhibited from leaving the enzyme's environment when the sensor is initially deployed.

The enzyme is preferably immobilized in the enzyme layer of the sensor. The enzyme may be wholly or partially encapsulated within the hydrophilic polymer and may be cross-linked or otherwise immobilized therein. The enzyme may be cross-linked or otherwise immobilized optionally together with at least one protein and/or natural or synthetic material.

The hydrophilic polymer of the enzyme layer may further include at least one protein and/or natural or synthetic material. For example, the hydrophilic polymer of the enzyme layer may further include, for example, serum albumins, polyallylamines, polyamines and the like, as well as combination thereof. However, the hydrophilic polymer of the enzyme layer may exclude serum albumins from bovine sources. Thus, in one aspect, other proteins or natural or synthetic materials may be substantially excluded from the enzyme layer. For example, the enzyme layer may be substantially free or completely absent bovine serum albumin. Bovine albumin-free compositions may be desirable for meeting various governmental regulatory requirements. Thus, in one aspect, the enzyme layer consists essentially of a hydrophilic polymer, a glucose oxidase and a sufficient amount of cross-linking agent, for example, a dialdehyde such as glutaraldehdye, to cross-link or otherwise immobilize the enzyme. In other aspect, the enzyme layer consists essentially of glucose oxidase, poly-N-vinylpyrrolidone and a sufficient amount of cross-linking agent to cross-link or otherwise immobilize the enzyme.

The enzyme layer thickness may be from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. Preferably, the enzyme layer is deposited by spray or dip coating, however, other methods of forming the enzyme layer may be used. The enzyme layer may be formed by dip coating and/or spray coating one or more layers at a predetermined concentration of the coating solution, insertion rate, dwell time, withdrawal rate, and/or desired thickness.

Optional Flux-limiting Membrane

The sensor or sensor assembly may optionally include a membrane disposed over the subsequent layers described above, where the membrane alters or changes the rate of flux of one or more of the analytes of interest (e.g., "flux-limiting membrane"). Although the following description is directed to a membrane for a glucose sensor, the membrane may be modified for other analytes and co-reactants as well. In one aspect, the sensor or sensor assembly includes a membrane as herein disclosed.

In one aspect, the membrane comprises a semi-permeable material that controls the flux of oxygen and glucose to the underlying enzyme layer, preferably providing oxygen in a non-rate-limiting excess. As a result, the upper limit of linearity of glucose measurement is extended to a much higher value than that which is achieved without the membrane. In one embodiment, the membrane exhibits an oxygen to glucose permeability ratio of from about 50:1 or less to about 400:1 or more, preferably about 200:1. Other flux-limiting layers may be used or combined, such as a membrane with both hydrophilic and hydrophobic polymeric regions, to control the diffusion of analyte and optionally co-analyte to an analyte sensor. For example, a suitable membrane may include a hydrophobic polymer matrix component such as a polyurethane, thermoplastic polycarbonate urethane, or polyetherurethaneurea. Hydrophobic-hydrophilic copolymers comprising polyethylene oxide segments in a polyurethane polymer that includes about 20% hydrophilic polyethylene oxide may be used. The polyethylene oxide portions of the copolymer are thermodynamically driven to separate from the hydrophobic portions (e.g., the urethane portions) of the copolymer and the hydrophobic polymer component. The 20% polyethylene oxide-based soft segment portion of the copolymer used to form the final blend affects the water pick-up and subsequent glucose permeability of the membrane.

In one aspect, non-polyurethane type materials, such as vinyl polymers, polyethers, polyesters, polyamides, inorganic polymers such as polysiloxanes and polycarbosiloxanes, natural polymers such as cellulosic and protein based materials, and mixtures or combinations thereof may be used as the flux-limiting layer.

In another aspect, the material that comprises the membrane may be a vinyl polymer appropriate for use in sensor devices having sufficient permeability to allow relevant compounds to pass through it, for example, to allow an oxygen molecule to pass through in order to reach the active enzyme or electrochemical electrodes. Examples of materials which may be used to make the membrane include vinyl polymers having vinyl ester monomeric units. In a preferred embodiment, a flux-limiting membrane comprises poly ethylene vinyl acetate (EVA polymer). In other aspects, the flux-limiting membrane comprises poly(methylmethacrylate-co-butyl methacrylate) blended with the EVA polymer. The EVA polymer or its blends may be cross-linked, for example, with diglycidyl ether. Films of EVA are very elastomeric, which may provide resiliency to the sensor for navigating a tortuous path, for example, into the venous anatomy of mammals.

In one aspect, the flux-limiting membrane substantially excludes condensation polymers such as silicone and urethane polymers and/or copolymers or blends thereof. Such excluded condensation polymers typically contain residual heavy metal catalytic material that may otherwise be toxic if leached and/or difficult to completely remove, thus rendering their use in such sensors undesirable for safety and/or cost.

The EVA polymer may be provided from a source having a composition anywhere from about 9 wt % vinyl acetate (EVA-9) to about 40 wt % vinyl acetate (EVA-40). The EVA polymer is preferably dissolved in a solvent for dispensing on the sensor or sensor assembly. The solvent should be chosen for its ability to dissolve EVA polymer, to promote adhesion to the sensor substrate and enzyme electrode, and to form a solution that may be effectively applied (e.g. spray-coated or dip coated). Solvents such as cyclohexanone, paraxylene, and tetrahydrofuran may be suitable for this purpose. The solution may include about 0.5 wt % to about 6.0 wt % of the EVA polymer. In addition, the solvent should be sufficiently volatile to evaporate without undue agitation to prevent issues with the underlying enzyme, but not so volatile as to create problems with the spray process. In a preferred embodiment, the vinyl acetate component of the flux-limiting membrane includes about 20% vinyl acetate. In preferred embodiments, the flux-limiting membrane is deposited onto the enzyme layer to yield a layer thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 5, 5.5 or 6 microns to about 6.5, 7, 7.5 or 8 microns. The flux-limiting membrane may be deposited onto the enzyme layer by spray coating or dip coating. In one aspect, the flux-limiting membrane is deposited on the enzyme layer by dip coating a solution of from about 1 wt. % to about 5 wt. % EVA polymer and from about 95 wt. % to about 99 wt. % solvent.

In one aspect, an electrochemical analyte sensor is provided comprising a flux-limiting membrane covering the enzyme layer, the interference layer and at least a portion of the electroactive surface. Thus, the sensor comprises at least one electroactive surface, an interference layer comprising an interference layer comprising a cellulosic derivative in contact with and at least partially covering at least a portion of the electroactive surface, an enzyme layer comprising a hydrophilic polymer, at least a portion of the enzyme layer in contact with and at least partially covering the interference layer, and a flux-limiting membrane covering the enzyme layer, the interference layer and encapsulating the enzyme layer, interferent layer and the electroactive surface. The buffering agent comprising at least one salt of acetate ion, carbonate ion, bicarbonate ion, or mixtures thereof is positioned (i) between the interferent layer and the electrode surface and/or (ii) over the interference layer, and/or (iii) associated with the enzyme layer. Additional layers, e.g., hydrophilic polymers, may be positioned (i) between the interferent layer and the electrode surface and/or (ii) over the interference layer, and such hydrophilic polymers may comprise the buffering agent.

Optional Bioactive Agents and Bioactive Layers

In some alternative embodiments, a bioactive agent may be optionally incorporated into the above described sensor system, such that the bioactive diffuses out into the biological environment adjacent to the sensor. Additionally or alternately, a bioactive agent may be administered locally at the exit-site or implantation-site. Suitable bioactive agents include those that modify the subject's tissue response to any of the sensor or components thereof. For example, bioactive agents may be selected from anti-inflammatory agents, anti-infective agents, anesthetics, inflammatory agents, growth factors, immunosuppressive agents, antiplatelet agents, anticoagulants, anti-proliferates, ACE inhibitors, cytotoxic agents, anti-barrier cell compounds, vascularization-inducing compounds, anti-sense molecules, or mixtures thereof. In some alternative embodiments, a bioactive agent layer may be used. The bioactive agent layer may be optionally incorporated into any of the above described layers, such that the bioactive diffuses out into the biological environment adjacent to the sensor. Additionally or alternately, a bioactive agent may be administered locally at the exit-site or implantation-site. Suitable bioactive agents include active agents that modify the subject's tissue response to any of the sensor or components thereof. For example, bioactive agents may be selected from anti-inflammatory agents, anti-infective agents, anesthetics, inflammatory agents, growth factors, immunosuppressive agents, antiplatelet agents, anti-coagulants, anti-proliferates, ACE inhibitors, cytotoxic agents, anti-barrier cell compounds, anti-vascularization-inducing compounds, anti-sense molecules, or mixtures thereof. The bioactive agent layer may be employed in the analyte sensor to prevent coagulation within or on the sensor (e.g., within or on the catheter or within or on the sensor). Suitable bioactive agents that function as anticoagulants for incorporation into or on the sensor include, but are not limited to, vitamin K antagonists (e.g., Acenocoumarol, Clorindione, Dicumarol (Dicoumarol), Diphenadione, Ethyl biscoumacetate, Phenprocoumon, Phenindione, Tioclomarol, or Warfarin), heparin group anticoagulants (e.g., Platelet aggregation inhibitors: Antithrombin III, Bemiparin, Dalteparin, Danaparoid, Enoxaparin, Heparin, Nadroparin, Parnaparin, Reviparin, Sulodexide, Tinzaparin), other platelet aggregation inhibitors (e.g., Abciximab, Acetylsalicylic acid (Aspirin), Aloxiprin, Beraprost, Ditazole, Carbasalate calcium, Cloricromen, Clopidogrel, Dipyridamole, Epoprostenol, Eptifibatide, Indobufen, Iloprost, Picotamide, Ticlopidine, Tirofiban, Treprostinil, Triflusal), enzymes (e.g., Alteplase, Ancrod, Anistreplase, Brinase, Drotrecogin alfa, Fibrinolysin, Protein C, Reteplase, Saruplase, Streptokinase, Tenecteplase, Urokinase), direct thrombin inhibitors (e.g., Argatroban, Bivalirudin, Desirudin, Lepirudin, Melagatran, Ximelagatran, other antithrombotics (e.g., Dabigatran, Defibrotide, Dermatan sulfate, Fondaparinux, Rivaroxaban) and the like. In one aspect, the bioactive agent layer comprises at least one active agent selected from the group consisting of vitamin K antagonists, heparin group anticoagulants, platelet aggregation inhibitors, enzymes, direct thrombin inhibitors, Dabigatran, Defibrotide, Dermatan sulfate, Fondaparinux, and Rivaroxaban.

The bioactive agent may be incorporated into the analyte sensing membrane of the described above. In some embodiments, the bioactive agent is incorporated at the time of manufacture of the analyte sensing membrane. For example, the bioactive agent can be blended prior to or subsequent to analyte sensing membrane manufacture, for example, by coating, imbibing, solvent-casting, or sorption of the bioactive agent into the analyte sensing membrane. Although the bioactive agent is preferably incorporated into the analyte sensing membrane, in some embodiments the bioactive agent can be administered concurrently with, prior to, or after insertion of the device comprising the sensor (e.g., intravascularly), for example, by oral administration, or locally, for example, by subcutaneous injection near the implantation site. A combination of the bioactive agent in the analyte sensing membrane and the bioactive agent administration locally and/or systemically may be preferred in certain aspects.

The bioactive agent may be incorporated or disposed only into or onto a portion of the analyte sensing membrane adjacent to the sensing region of the device, over the entire surface of the device except over the sensing region, or any combination thereof. Such arrangement of bioactive agent may be helpful in controlling different mechanisms and/or stages of thrombus formation. However, the bioactive agent may be incorporated into the analyte sensing membrane, so that the bioactive agent can diffuse through the analyte sensing membrane and into the host circulatory system. The bioactive agent can be deposited in or on the analyte sensing membrane, for example, by coating, filling, or solvent casting. The bioactive agent can be incorporated into a polymer using techniques such as described above, and the polymer can be used to form one of the layers of the analyte sensing membrane, coatings on the analyte sensing membrane, portions of the analyte sensing membrane, and/or any portion of the sensor.

A carrier may be used for the bioactive agent. The carrier may include one or more of collagen, a particulate matrix, a resorbable or non-resorbable matrix, a controlled-release matrix, and/or a gel. The carrier may include a reservoir encapsulating a microcapsule comprising a bioactive agent. The bioactive agent may be cross-linked with the analyte sensing membrane or sorbed into the analyte sensing membrane, for example, by adsorption, absorption, or imbibing.

The bioactive agents can be chosen for short-term release to aid or overcome factors associated with short-term effects (e.g., acute inflammation and/or thrombosis) of sensor insertion, for example. The bioactive agents may be chosen for long-term release to aid or overcome factors associated with long-term effects, for example, chronic inflammation or build-up of fibrotic tissue and/or plaque material. The bioactive agents may combine short- and long-term release to provide the benefits of both. Thus, the bioactive agents may be provided in a controlled, sustained or extended release form, wherein "controlled," "sustained," or "extended" release is inclusive of continuous or discontinuous, linear or non-linear release profiles. This can be accomplished using one or more types of polymer compositions, drug loadings, selections of excipients or degradation enhancers, or other modifications, administered alone, in combination or sequentially to produce the desired effect.

The bioactive agent can be incorporated into a hydrogel and coated or otherwise deposited in or on the analyte sensing membrane. Some hydrogels suitable for use include cross-linked, hydrophilic, three-dimensional polymer networks that are permeable to the bioactive agent and/or release the bioactive agent based on an external stimulus.

The amount of bioactive agent into the analyte sensing membrane can depend upon several external variables. For example, the bioactive agent dosage and duration can vary with the intended use of the analyte sensing membrane, for example, the intended length of use of the device; differences in effective dose of bioactive agent among patients in the; location and administration of the bioactive agent; and release rates associated with bioactive agents. One skilled in the art will appreciate the variability in loading levels of the bioactive agent for at least the reasons described above.

When the bioactive agent is incorporated into the analyte sensing membrane without a carrier, the level of loading of the bioactive agent into the analyte sensing membrane can vary depending upon the chemical and/or physical nature of the bioactive agent. The level of loading of the bioactive agent is preferably sufficiently high such that a biological effect (e.g., thrombosis prevention) is obtained. The level of loading (based on the weight of bioactive agent(s), analyte sensing membrane, and other substances present) is from about 1 ppm or less to about 1000 ppm or more, preferably from about 2, 3, 4, or 5 ppm up to about 10, 25, 50, 75, 100, 200, 300, 400, 500, 600, 700, 800, or 900 ppm. In certain embodiments, the level of loading can be 1 wt. % or less up to about 50 wt. % or more, preferably from about 2, 3, 4, 5, 6, 7, 8, 9, 10, 15, or 20 wt. % up to about 25, 30, 35, 40, or 45 wt. %.

When the bioactive agent is incorporated into the analyte sensing membrane with a carrier, the carrier concentration can be optimized by loading with one or more test loadings of the bioactive agent. The carrier may contain from about 0.1 or less to about 50 wt. % or more of the bioactive agent(s), preferably from about 0.2, 0.3, 0.4, 0.5, 0.6, 0.7, 0.8, or 0.9 wt. % to about 6, 7, 8, 9, 10, 15, 20, 25, 30, 35, 40, or 45 wt. % or more bioactive agent(s), more preferably from about 1, 2, or 3 wt. % to about 4 or 5 wt. % of the bioactive agent(s). Substances that are not bioactive and/or act synergistically with the bioactive agent can also be used.

Flexible Substrate Sensor Assembly Adapted for Intravenous Insertion

In one aspect, an electrochemical analyte sensor assembly may be configured for an intravenous insertion to a vascular system of a subject. In order to accommodate the sensor within the confined space of a device suitable for intravenous insertion, the sensor assembly may comprise a flexible substrate, such as a flex circuit. For example, the flexible substrate of the flex circuit may be configured as a thin conductive electrodes coated on a non-conductive material such as a thermoplastic or thermoset. Conductive traces may be formed on the non-conductive material and electrically coupled to the thin conductive electrodes. The electrodes of the flex circuit may be as described above.

The flex circuit may comprise at least one reference electrode and at least one working electrode, the at least one working electrode having an electroactive surface capable of providing a detectable electrical output upon interaction with an electrochemically detectable species. The flex circuit may further comprise at least one counter electrode. In one aspect, the flex circuit contains two or more working electrodes and two or more counter electrodes. In one aspect, the flex circuit contains two or more working electrodes, at least one blank electrode and at least one counter electrode.

Medical devices adaptable to the sensor assembly as described above include, but are not limited to a central venous catheter (CVC), a pulmonary artery catheter (PAC), a probe for insertion through a CVC or PAC or through a peripheral IV catheter, a peripherally inserted catheter (PICC), Swan-Ganz catheter, an introducer or an attachment to a Venous Arterial blood Management Protection (VAMP) system. Any size/type of Central Venous Catheter (CVC) or intravenous devices may be used or adapted for use with the sensor assembly.

For the foregoing discussion, the implementation of the sensor or sensor assembly is disclosed as being placed within a catheter, however, other devices as described above are envisaged and incorporated in aspects of the invention. The sensor assembly will preferably be applied to the catheter so as to be flush with the OD of the catheter tubing. This may be accomplished, for example, by thermally deforming the OD of the tubing to provide a recess for the sensor. The sensor assembly may be bonded in place, and sealed with an adhesive (ie. urethane, 2-part epoxy, acrylic, etc.) that will resist bending/peeling, and adhere to the urethane CVC tubing, as well as the materials of the sensor. Small diameter electrical wires may be attached to the sensor assembly by soldering, resistance welding, or conductive epoxy. These wires may travel from the proximal end of the sensor, through one of the catheter lumens, and then to the proximal end of the catheter. At this point, the wires may be soldered to an electrical connector.

The sensor assembly as disclosed herein can be added to a catheter in a variety of ways. For example, an opening may be provided in the catheter body and a sensor or sensor assembly may be mounted inside the lumen at the opening so that the sensor would have direct blood contact. In one aspect, the sensor or sensor assembly may be positioned proximal to all the infusion ports of the catheter. In this configuration, the sensor would be prevented from or minimized in measuring otherwise detectable infusate concentration instead of the blood concentration of the analyte. Another aspect, an attachment method may be an indentation on the outside of the catheter body and to secure the sensor inside the indentation. This may have the added advantage of partially isolating the sensor from the temperature effects of any added infusate. Each end of the recess may have a skived opening to 1) secure the distal end of the sensor and 2) allow the lumen to carry the sensor wires to the connector at the proximal end of the catheter.

Preferably, the location of the sensor assembly in the catheter will be proximal (upstream) of any infusion ports to prevent or minimize IV solutions from affecting analyte measurements. In one aspect, the sensor assembly may be about 2.0 mm or more proximal to any of the infusion ports of the catheter.

In another aspect, the sensor assembly may be configured such that flushing of the catheter (ie. saline solution) may be employed in order to allow the sensor assembly to be cleared of any material that may interfere with its function.

Sterilization of the Sensor or Sensor Assembly

Generally, the sensor or the sensor assembly as well as the device that the sensor is adapted to are sterilized before use, for example, in a subject. Sterilization may be achieved using radiation (e.g., electron beam or gamma radiation), ethylene oxide or flash-UV sterilization, or other means know in the art.

Disposable portions, if any, of the sensor, sensor assembly or devices adapted to receive and contain the sensor preferably will be sterilized, for example using e-beam or gamma radiation or other know methods. The fully assembled device or any of the disposable components may be packaged inside a sealed non-breathable container or pouch.

Referring now to the Figures, FIG. 1 is an amperometric sensor 11 in the form of a flex circuit that incorporates a sensor embodiment disclosed herein. The sensor or sensor 11 may be formed on a substrate 13 (e.g., a flex substrate, such as copper foil laminated with polyimide). One or more electrodes 15, 17 and 19 may be attached or bonded to a surface of the substrate 13 or may be positioned in recessed areas of the substrate. The sensor 11 is shown with a reference electrode 15, a counter electrode 17, and a working electrode 19. In another embodiment, one or more additional working electrodes may be included on the substrate 13. Electrical wires 210 may transmit power to the electrodes for sustaining an oxidation or reduction reaction, and may also carry signal currents to a detection circuit (not shown) indicative of a parameter being measured. The parameter being measured may be any analyte of interest that occurs in, or may be derived from, blood chemistry. In one embodiment, the analyte of interest may be hydrogen peroxide, formed from reaction of glucose with glucose oxidase, thus having a concentration that is proportional to blood glucose concentration.

Figure 2:
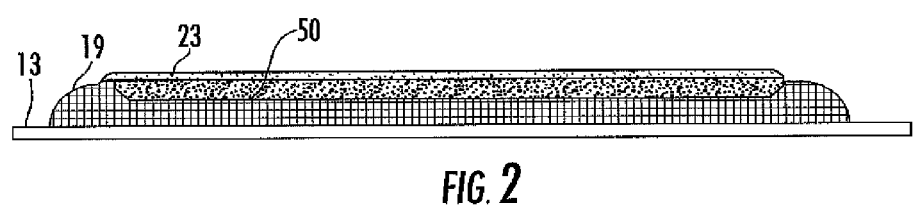
FIG. 2 is a side cross-sectional view of a working electrode portion of the sensor of shown prior to application of a flux-limiting membrane according to an embodiment of the invention.

FIG. 2 depicts a cross-sectional side view of a portion of substrate 13 in the vicinity of the working electrode 19 of an embodiment disclosed herein. The working electrode 19 may be at least partially coated with an interference layer 50. Interference layer 50 may be at least partially coated with an enzyme layer 23 that is selected to chemically react when the sensor is exposed to certain reactants, for example, found in the bloodstream. For example, in an embodiment for a glucose sensor, enzyme layer 23 may contain glucose oxidase, such as may be derived from *Aspergillus niger* (EC 1.1.3.4), type II or type VII. The general shape of the electrodes may be concave (as shown), or may be flat or convex, such as electrodes shaped to conform to recesses in the substrate.

Figure 3:
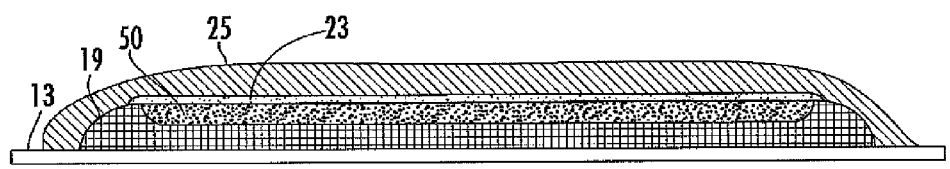
FIG. 3 is a cross-sectional view of the working electrode portion of the sensor as in FIG. 2, shown after application of the flux-limiting membrane according to an embodiment of the invention.

FIG. 3 shows a cross sectional side view of the working electrode site on the sensor substrate 13 further comprising flux-limiting membrane 25 covering (encapsulating) enzyme layer 23 and interference layer 50 and at least a portion of electrode 19. Flux-limiting membrane 25 may selectively allow diffusion, from blood to the enzyme layer 23, a blood component that reacts with the enzyme. In a glucose sensor embodiment, the flux-limiting membrane 25 passes an abundance of oxygen, and selectively limits glucose, to the enzyme layer 23. In addition, a flux-limiting membrane 25 that has adhesive properties may mechanically seal the enzyme layer 23 to the sub-layers and/or working electrode 19, and may also seal the working electrode 19 to the sensor substrate 13. It is herein disclosed that a flux-limiting membrane formed from an EVA polymer may serve as a flux limiter at the top of the electrode, but also serve as a sealant or encapsulant at the enzyme/electrode boundary and at the electrode/substrate boundary. An additional biocompatible layer (not shown), including a biocompatible anti-thrombotic substance such as heparin, may be added onto the flux-limiting membrane 25.

Figure 4:
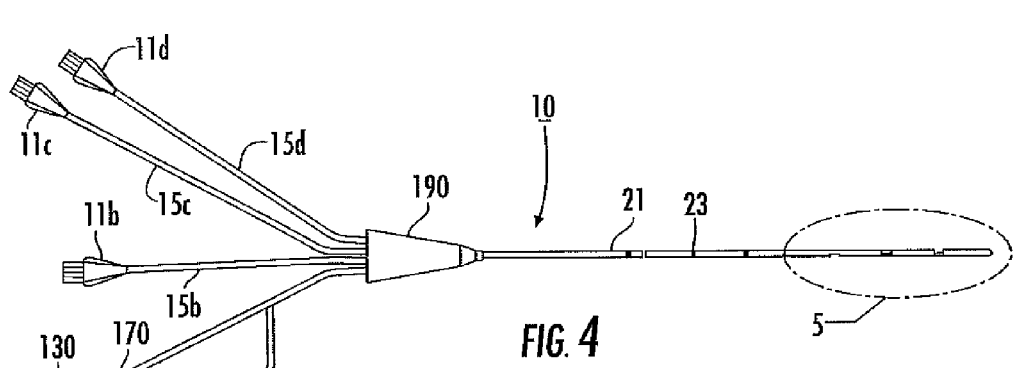
FIG. 4 is a side view of a multilumen catheter with a sensor assembly according to an embodiment of the invention.
Figure 5:
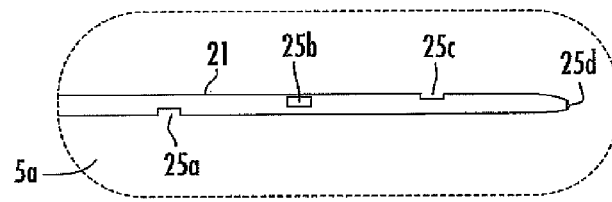
FIG. 5 is a detail of the distal end of the multilumen catheter of FIG. 4 according to an embodiment of the invention.

Referring now to FIGS. 4-5, aspects of the sensor adapted to a central line catheter with a sensor or sensor assembly are discussed as exemplary embodiments, without limitation to any particular intravenous device. FIG. 4 shows a sensor assembly within a multilumen catheter. The catheter assembly 10 may include multiple infusion ports 11a, 11b, 11c, 11d and one or more electrical connectors 130 at its most proximal end. A lumen 15a, 15b, 15c or 15d may connect each infusion port 11a, 11b, 11c, or 11d, respectively, to a junction 190. Similarly, the conduit 170 may connect an electrical connector 130 to the junction 190, and may terminate at junction 190, or at one of the lumens 15a-15d (as shown). Although the particular embodiment shown in FIG. 4 is a multilumen catheter having four lumens and one electrical connector, other embodiments having other combinations of lumens and connectors are possible, including a single lumen catheter, a catheter having multiple electrical connectors, etc. In another embodiment, one of the lumens and the electrical connector may be reserved for a probe or other sensor mounting device, or one of the lumens may be open at its proximal end and designated for insertion of the probe or sensor mounting device.

Distal end 5 of the catheter assembly 10 is shown in greater detail in FIG. 5 in exploded section 5a. At one or more intermediate locations along the distal end, the tube 21 may define one or more ports formed through its outer wall. These may include the intermediate ports 25a, 25b, and 25c, and an end port 25d that may be formed at the distal tip of tube 21. Each port 25a-25d may correspond respectively to one of the lumens 15a-15d. That is, each lumen may define an independent channel extending from one of the infusion ports 11a-11d to one of the tube ports 25a-25d. Sensor may be presented to the sensing environment via positioning at one or more of the ports to provide contact with the medium to be analyzed.

Central line catheters may be known in the art and typically used in the Intensive Care Unit (ICU)/Emergency Room of a hospital to deliver medications through one or more lumens of the catheter to the patient (different lumens for different medications). A central line catheter is typically connected to an infusion device (e.g. infusion pump, IV drip, or syringe port) on one end and the other end inserted in one of the main arteries or veins near the patient's heart to deliver the medications. The infusion device delivers medications, such as, but not limited to, saline, drugs, vitamins, medication, proteins, peptides, insulin, neural transmitters, or the like, as needed to the patient. In alternative embodiments, the central line catheter may be used in any body space or vessel such as intraperitoneal areas, lymph glands, the subcutaneous, the lungs, the digestive tract, or the like and may determine the analyte or therapy in body fluids other than blood. The central line catheter may be a double lumen catheter. In one aspect, an analyte sensor is built into one lumen of a central line catheter and is used for determining characteristic levels in the blood and/or bodily fluids of the user. However, it will be recognized that further embodiments may be used to determine the levels of other agents, characteristics or compositions, such as hormones, cholesterol, medications, concentrations, viral loads (e.g., HIV), or the like. Therefore, although aspects disclosed herein may be primarily described in the context of glucose sensors used in the treatment of diabetes/diabetic symptoms, the aspects disclosed may be applicable to a wide variety of patient treatment programs where a physiological characteristic is monitored in an ICU, including but not limited to blood gases, pH, temperature and other analytes of interest in the vascular system.

In another aspect, a method of intravenously measuring an analyte in a subject is provided. The method comprises providing a catheter comprising the sensor assembly as described herein and introducing the catheter into the vascular system of a subject. The method further comprises measuring an analyte.

EXAMPLES

Sensors may be prepared comprising a salt comprising acetate ion, carbonate ion, bicarbonate ion, or mixtures thereof as follows: (i) deposited as a dried layer between the electroactive surface and the interference layer; (ii) deposited as a dried layer between the interference layer and an enzyme layer; (iii) associated with a hydrophilic polymer layer positioned either between the electrode surface and the interference layer or between the interference layer and an enzyme layer; (iv) associated with the enzyme layer; or (v) any or all combinations of (i)-(iv). In vitro, electrochemical analyte sensor testing methods for testing, validating, or improving the sensors were carried out by contacting an aqueous solution comprising a salt having acetate ion, carbonate ion, bicarbonate ion, or mixtures thereof.

Thus, as a prophetic example, to a electroactive surface of a fabricated working electrode (e.g., carbon/Pt ink or Pt; oxygen plasma cleaned) treated with a 3 wt % ethanol solution of 3-glycidoxypropyl trimethoxysilane and dried, may be deposited an aqueous solution comprising a salt having acetate ion, carbonate ion, bicarbonate ion, or mixtures thereof of at least 20 mM (optionally also comprising 1×PBS: 137 mM NaCl, 2.7 mM KCl, 10 mM phosphate) and dried. To the dried salt layer may be coated an interference layer of 0.2 wt % CAB solution in cyclohexanone and dried for 15 minutes @ 60 C. A second salt layer may be deposited on the CAB layer as just described. An enzyme layer solution of 30 mg GOx and 70 mg BSA added to 2 microliters of 2.5 wt % K90 PVP in acetate buffered DI water may be deposited on the CAB layer (or optional second dried salt layer). The pH of the enzyme solution may be adjusted to about 6 with 1M sodium bicarbonate. 25% glutaraldehyde solution (10 microliters for each ml of solution) may optionally be added to the enzyme solution prior to deposition. A flux-limiting membrane comprising a 2 wt % EVA in xylene may then be sprayed (1×-4×) over the enzyme layer and dried for 15 minutes @ 60 C.

A second prophetic example is as follows. To the electroactive surface of a working electrode (e.g., carbon/Pt ink or Pt; oxygen plasma cleaned) treated with a 3 wt % ethanol solution of 3-glycidoxypropyl trimethoxysilane and dried, may be deposited an interference layer of 0.2 wt % CAB solution in cyclohexanone and dried for 15 minutes @ 60 C. To the CAB layer may be deposited an aqueous solution comprising a salt having acetate ion, carbonate ion, bicarbonate ion, or mixtures thereof of at least 20 mM (optionally also comprising 1×PBS: 137 mM NaCl, 2.7 mM KCl, 10 mM phosphate) and dried. To the dried salt layer may be coated an enzyme layer (optionally comprising a salt having at least 20 mM of acetate ion, carbonate ion, bicarbonate ion, or mixtures thereof) from a solution of 30 mg GOx and 70 mg BSA added to 2 microliters of 2.5 wt % K90 PVP in a buffered DI water solution. The pH of the enzyme coating solution may adjusted to about 6 with 1M sodium bicarbonate. 25% glutaraldehyde solution (10 microliters for each ml of solution) may optionally be added to the enzyme solution prior to deposition on the dried salt layer. A flux-limiting membrane comprising a 2 wt % EVA in xylene may be sprayed (1×-4×) over the enzyme layer of these prophetic examples and dried for 15 minutes @ 60 C.

A third prophetic example is as follows. To the electroactive surface of a working electrode treated with a 3 wt % ethanol solution of 3-glycidoxypropyl trimethoxysilane and dried, may be deposited an interference layer of 0.2 wt % CAB solution in cyclohexanone and dried for 15 minutes @ 60 C. The enzyme layer comprising a salt having at least 20 mM of acetate ion, carbonate ion, bicarbonate ion, or mixtures thereof (optionally also comprising 1×PBS: 137 mM NaCl, 2.7 mM KCl, 10 mM phosphate), may be deposited to the above layer from a solution of 30 mg GOx and 70 mg BSA was added to 2 microliters of 2.5 wt % K90 PVP in a buffered DI water solution. The pH of the solution may adjusted to about 6 with 1M sodium bicarbonate. 25% glutaraldehyde solution (10 microliters for each ml of solution) may optionally be combined prior to deposition on the CAB layer. Likewise, an enzyme layer comprising a salt having at least 100 mM of acetate ion, carbonate ion, bicarbonate ion, or mixtures thereof (optionally also comprising 1×PBS: 137 mM NaCl, 2.7 mM KCl, 10 mM phosphate), may be deposited to the above layer from a solution of 30 mg GOx and 70 mg BSA was added to 2 microliters of 2.5 wt % K90 PVP in a buffered DI water solution. The pH of the solution may be adjusted to about 6 with 1M sodium bicarbonate. Glutaraldehyde solution 25 wt % (10 microliters for each ml of solution) may optionally be combined with the enzyme solution prior to deposition on the CAB layer. A flux-limiting membrane comprising a 2 wt % EVA in xylene may be sprayed (1×-4×) over the enzyme layer of these prophetic examples and dried for 15 minutes @ 60 C.

In vitro test solutions for testing, validating, or improving electrochemical analyte sensors were prepared from salts having acetate ion, carbonate ion, bicarbonate ion, or mixtures thereof (e.g., sodium bicarbonate, optionally also comprising 1×PBS: 137 mM NaCl, 2.7 mM KCl, 10 mM phosphate) in distilled water (dH2O). Exemplary electrochemical sensors used for testing, validating, or improving, were prepared with membrane structure that may be designated having the structure "electrode/CAB/PVP-GOx/EVA" prepared as described above without using acetate ion, carbonate ion, or bicarbonate ion salts, or dried salt layers thereof.

Figure 6A:
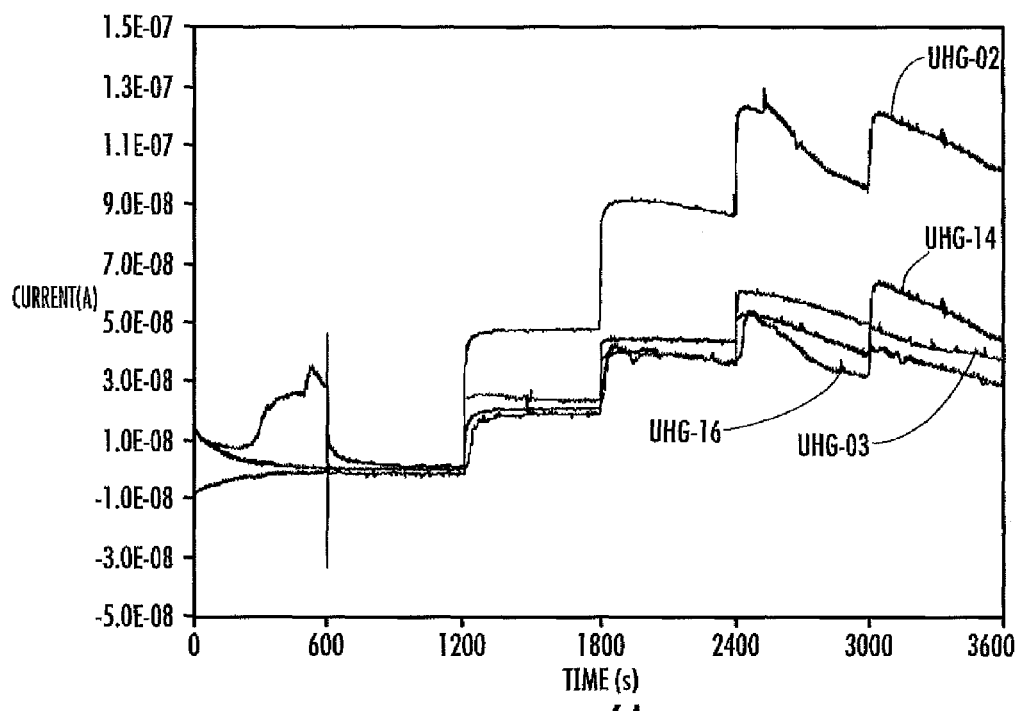
FIGS. 6A and 6B are graphs of current output verses time for a collection of test sensors using a 1×PBS and a 10×PBS control buffering system, respectively.
Figure 6B:
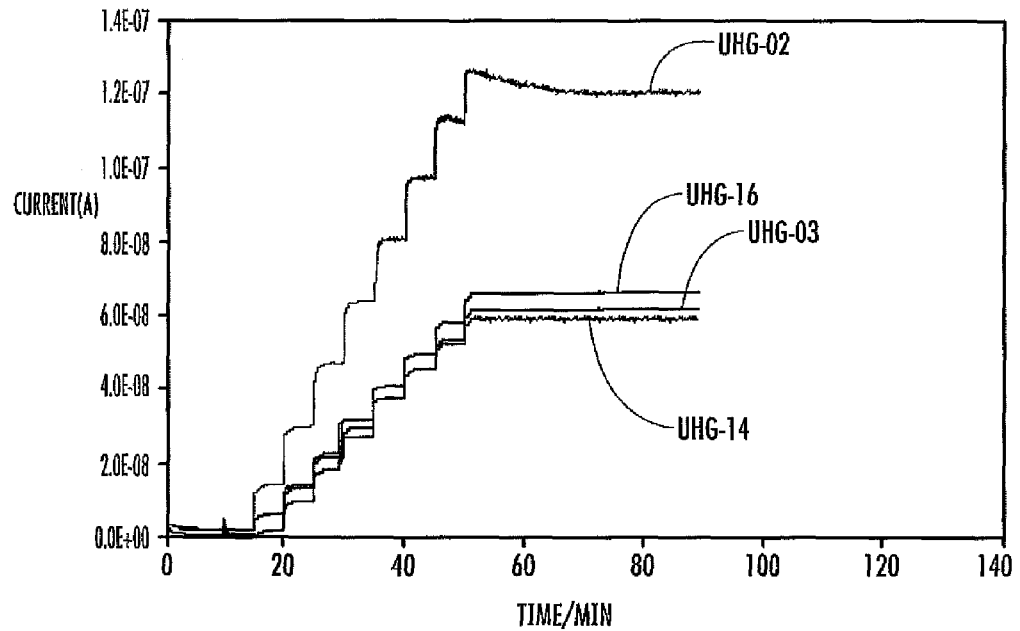

Referring to FIGS. 6A-6B, graphs of current output verses time to known glucose concentrations for a collection of test sensors (UHG-02, 03, 14 and 16) using a 1×PBS control buffering system and a 10×PBS control buffering system, respectively, are presented. The x-axis represents time, the y-axis represents current. The sensors were connected to a potentiostat using a working electrode potential of about 850 mV for 10 minutes before adjusting the voltage to the working potential of about 650 mV .vs. Ag/AgCl prior to testing. The sensors were contacted with the PBS solutions at a pH of about 7.4 at 37° C. and glucose solutions of incremental higher concentration (+50 mg/dL each) were added. The step change in the graphs represent a change in concentration of glucose. As seen in the graphs, the current of the sensors in the 1×PBS buffering system does not maintain linearity at high glucose concentrations (drift), and the current in the 10×PBS buffering system, while slightly improved over the 1×PBS system, still fails to consistently maintain linearity at high glucose concentrations (drift).

Figure 7:
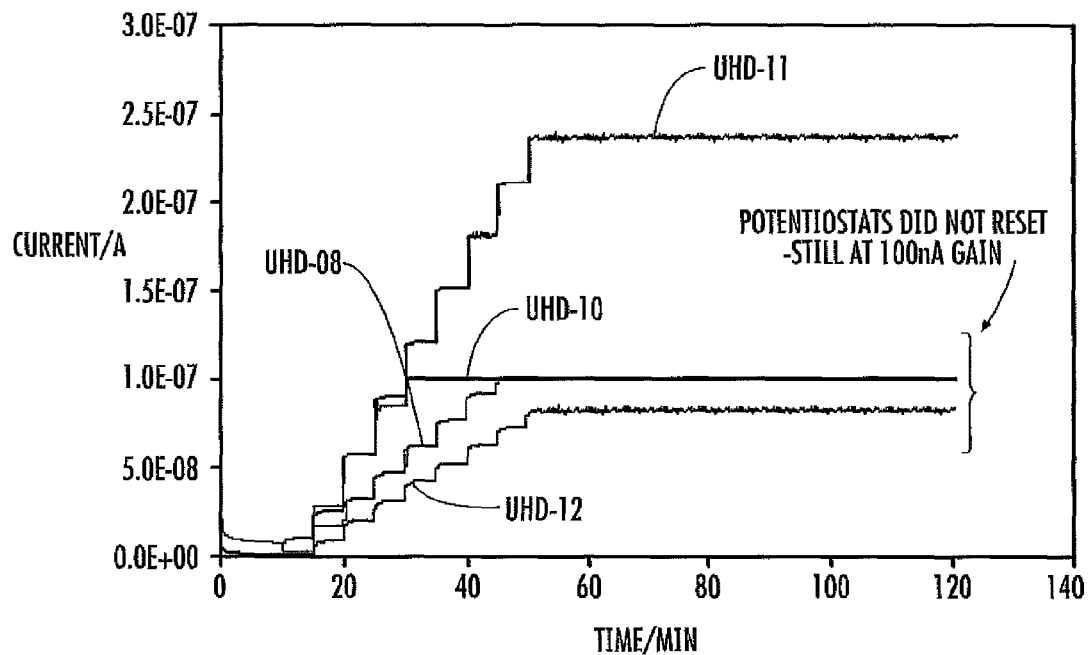
FIG. 7 depicts a graph of current output verses time for a collection of test sensors using a buffering system at 100 mM bicarbonate, as herein disclosed and described.

In contrast, as shown in FIG. 7 depicting current output verses time to known glucose concentrations for a collection of test sensors (UHD-08, 10, 11, and 12) using 100 mM sodium carbonate/PBS buffering system, maintains linearity without significant drift of signal at high glucose concentrations, and maintains linearity for extended periods of time. The x-axis represents time, the y-axis represents current. The sensors were connected to a potentiostat using a working electrode potential of about 850 mV for 10 minutes before adjusting the voltage to the working potential of about 650 mV .vs. Ag/AgCl prior to testing. The sensors were contacted with a bicarbonate/PBS solution at a pH of about 7.4 at 37° C. and glucose solutions of incremental higher concentration (+50 mg/dL each) were added. The step change in the graphs represent a change in concentration of glucose. Certain of the individual test sensors acquired data while exceeding the set gain of 100 nA ("flat-liners"), and are thus so indicated by the arrow. Similar results were obtained for sensors tested using 20 mM sodium carbonate/PBS buffering system (data not shown).

Figure 8:
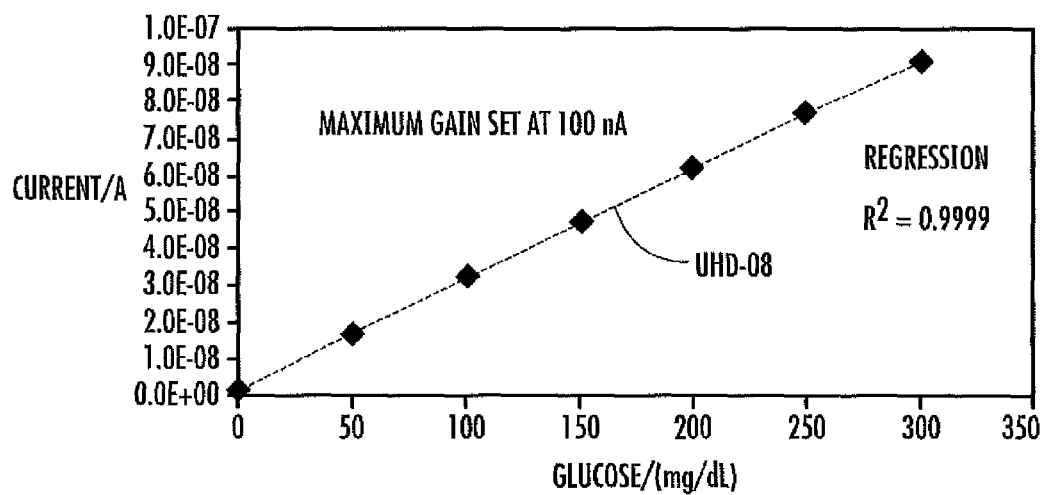
FIGS. 8-10 are calibration curves and calculated regression lines of current output verses glucose concentration corresponding to the current output verses time data for the individual sensors depicted in FIG. 7.
Figure 9:
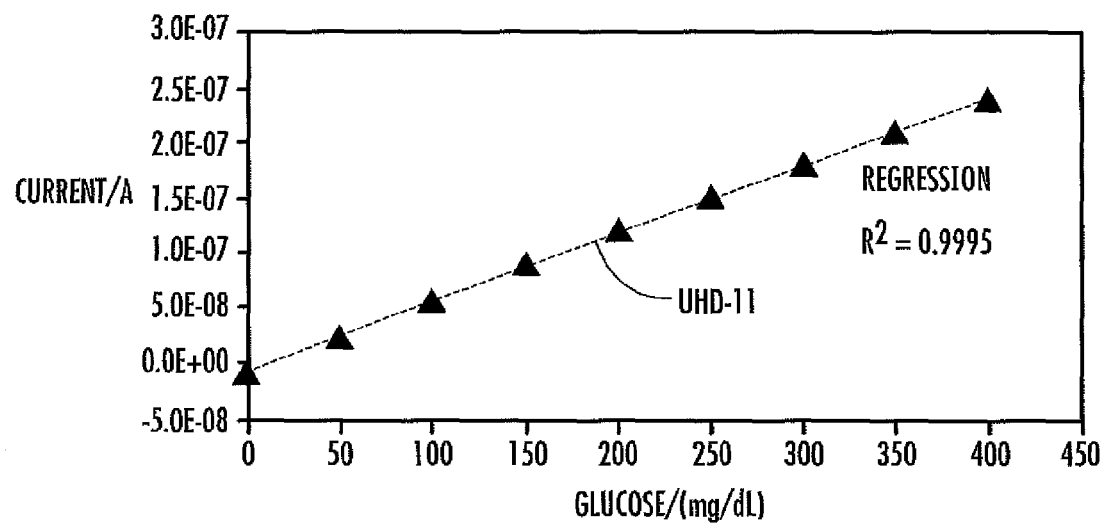
Figure 10:
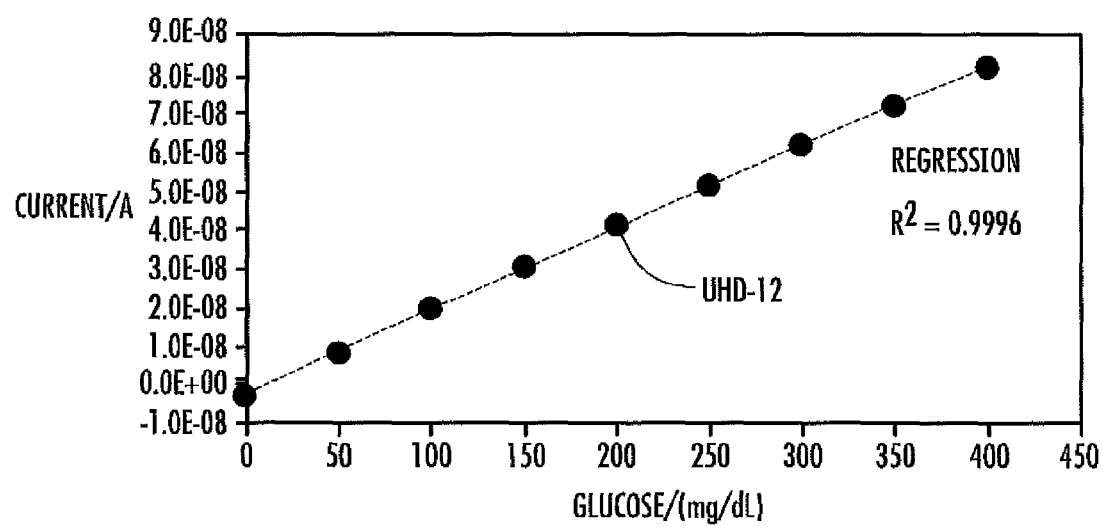

FIGS. 8-10 are graphical representations showing calibration curves of the individual glucose sensors based on the data depicted in FIG. 7. In these graphs, regression lines are dotted and the sensor-derived data points are indicated by geometrical symbols. These data show excellent linearity of the sensors tested in carbonate/PBS medium.

Figure 11:
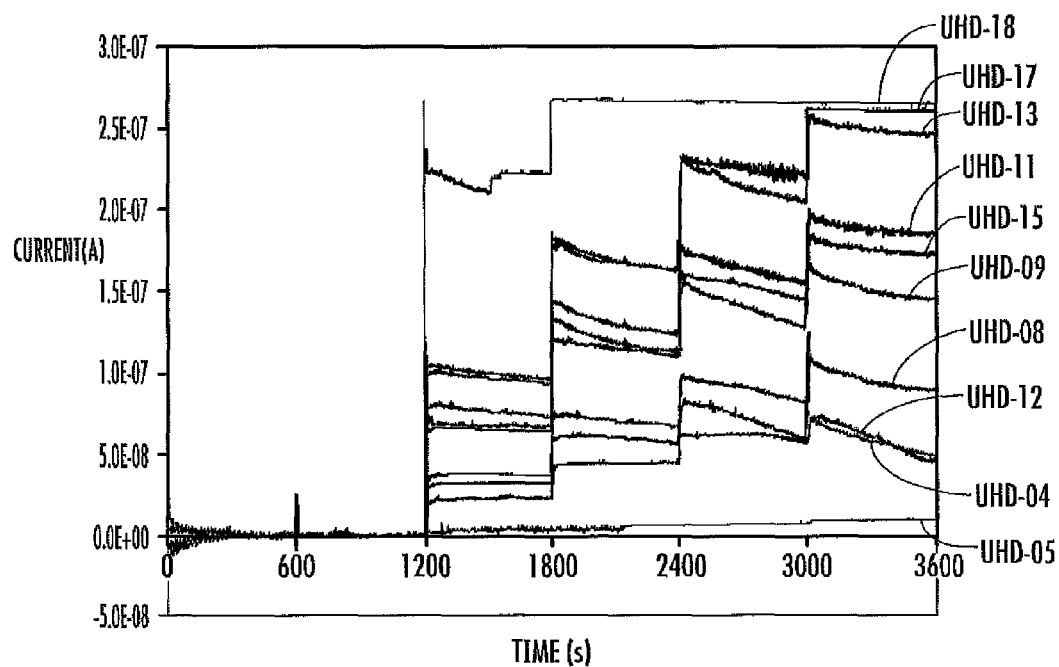
FIG. 11 is a graph of current output verses time for a collection of test sensors using a PBS control buffering system.

FIG. 11 is a graph of current output verses time to known glucose concentrations for an additional collection of test sensors (Uhd-04, 05, 08, 09, 11, 12, 13, 15, 17, and 19) using a 1×PBS control with results similar to that seen in FIG. 6A. In these graphs, the x-axis represents time, the y-axis represents current. The sensors were connected to a potentiostat using a working electrode potential of about 850 mV for 10 minutes before adjusting the voltage to the working potential of about 650 mV .vs. Ag/AgCl prior to testing. The sensors were subjected to the 1×PBS solution at pH 7.4 at 37° C. As seen in the graphs, the current continues to decrease over time at constant glucose concentration, in particular, at the higher concentrations.

Figure 12:
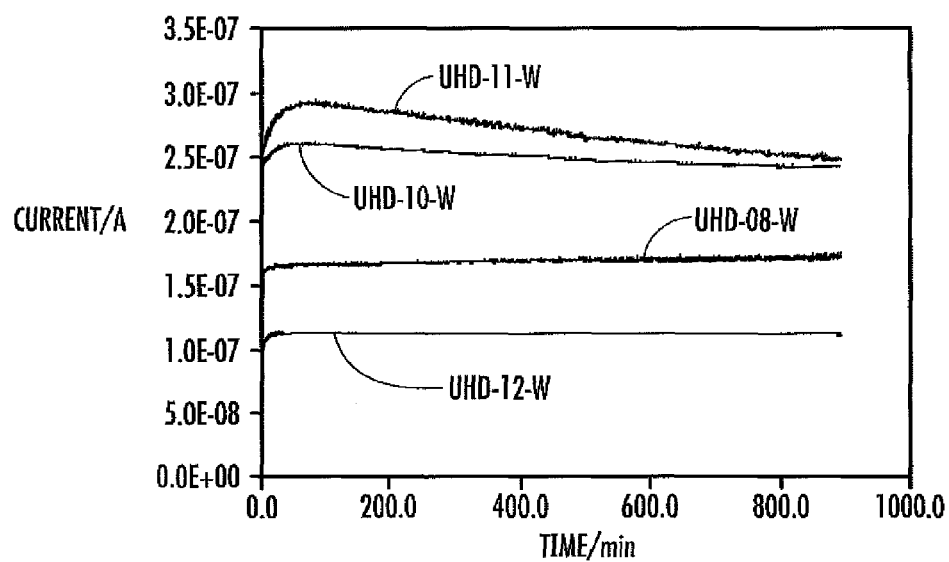
FIG. 12 is a graph of current output verses time for a collection of test sensors held at high analyte concentration using a buffering system as herein disclosed and described.
Figure 13:
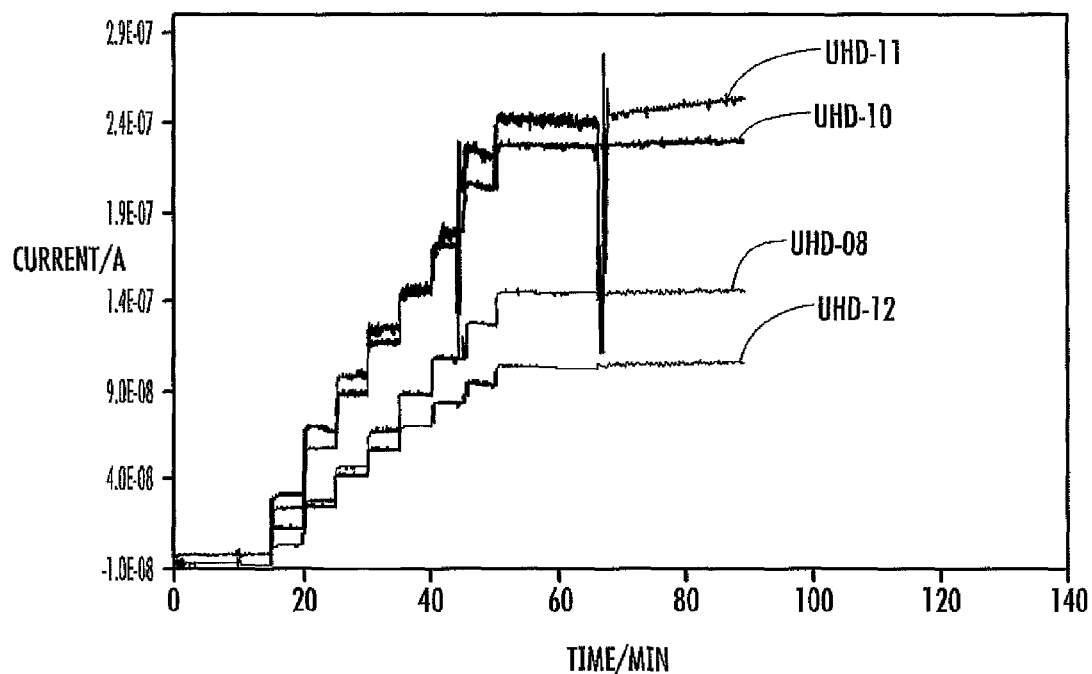
FIGS. 13-17 are calibration curves with associated calculated regression lines of current output verses glucose concentration corresponding to each of the individual sensors depicted in FIG. 12.
Figure 14:
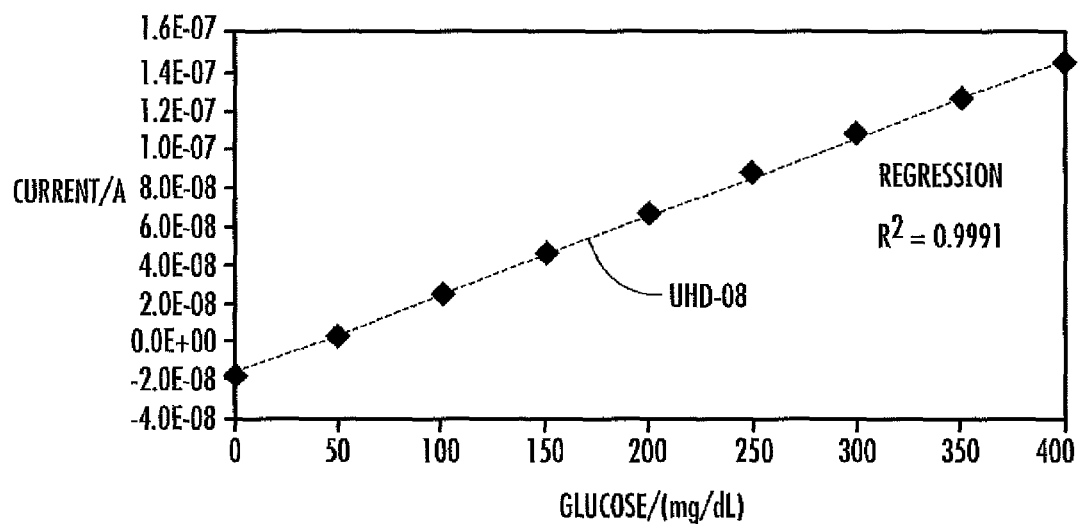
Figure 15:
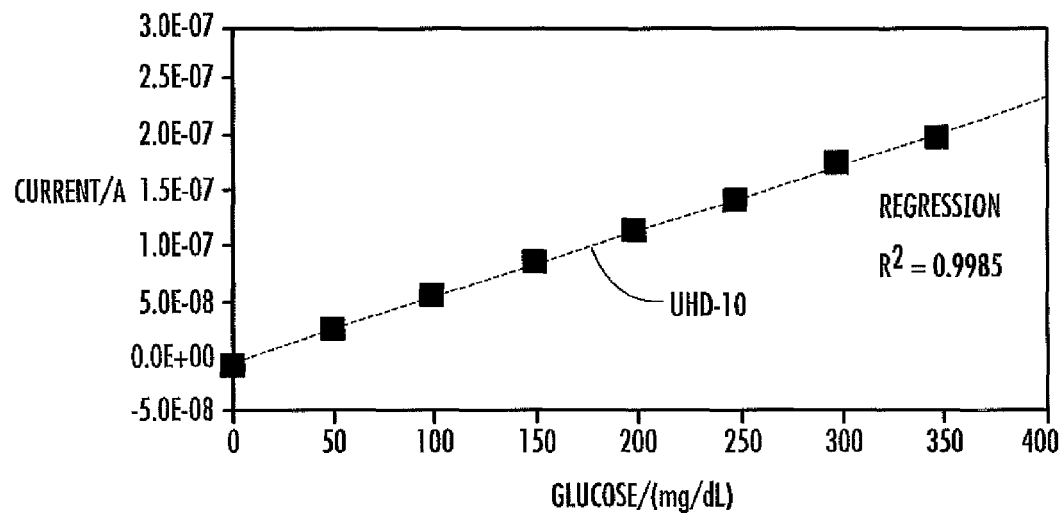
Figure 16:
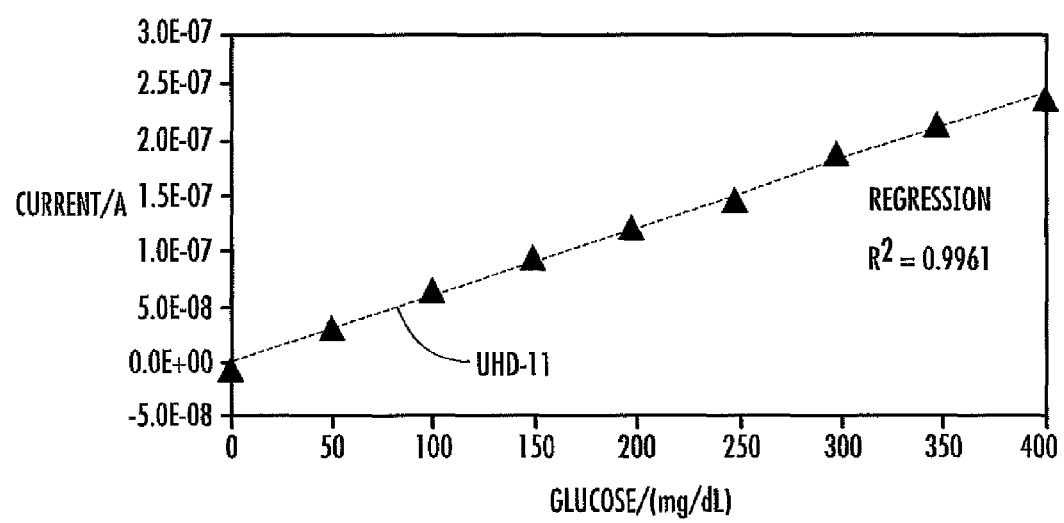
Figure 17:
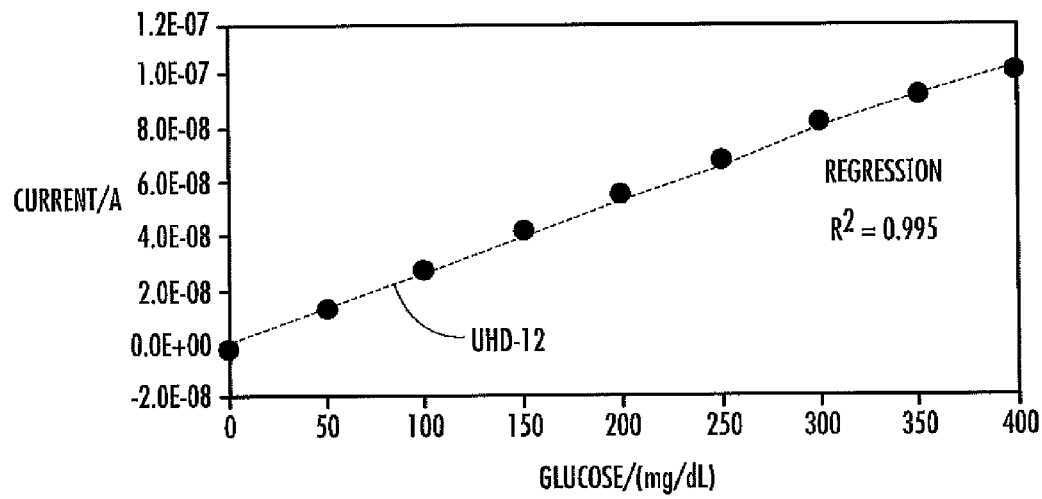
Figure 18:
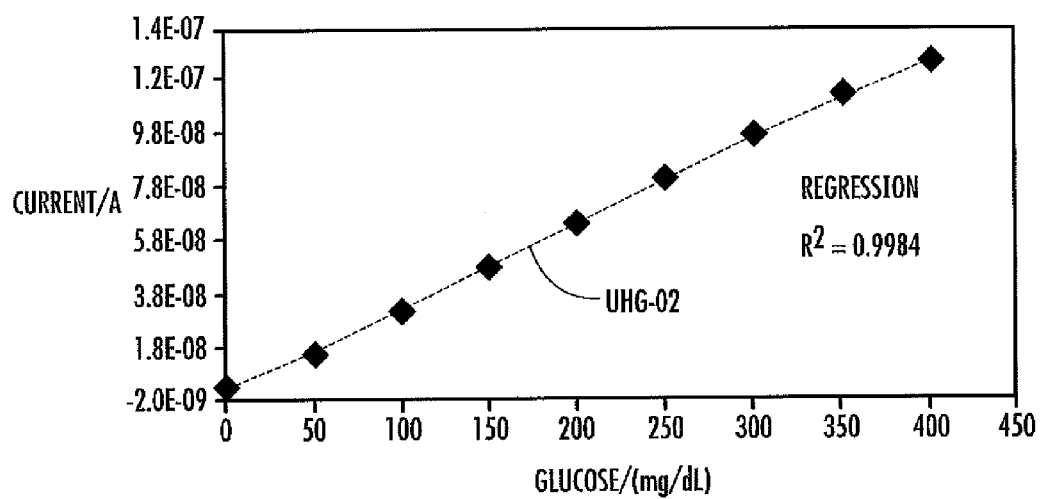
FIGS. 18-21 are calibration curves with associated calculated regression lines of current output verses glucose concentration corresponding to individual control sensors based on the data depicted in FIG. 6B using a 10×PBS control buffering system.
Figure 19:
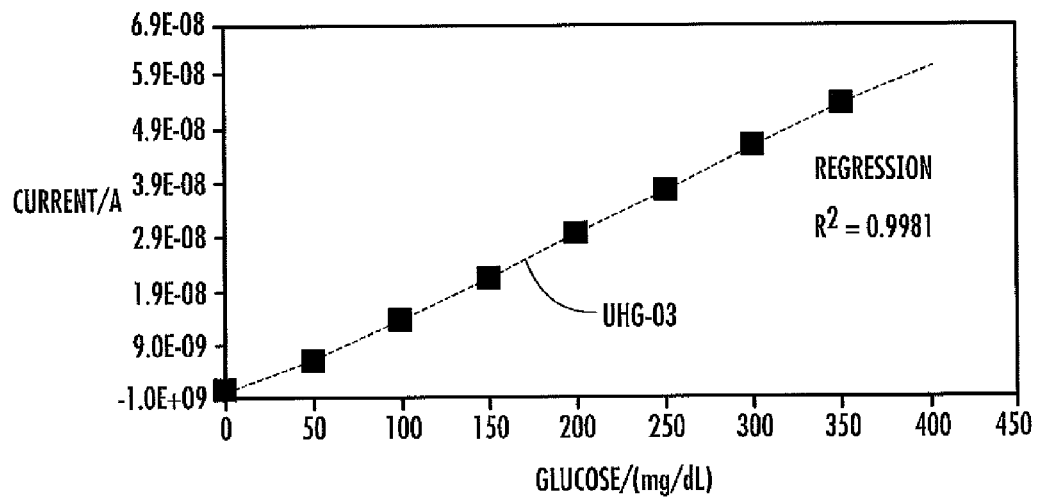
Figure 20:
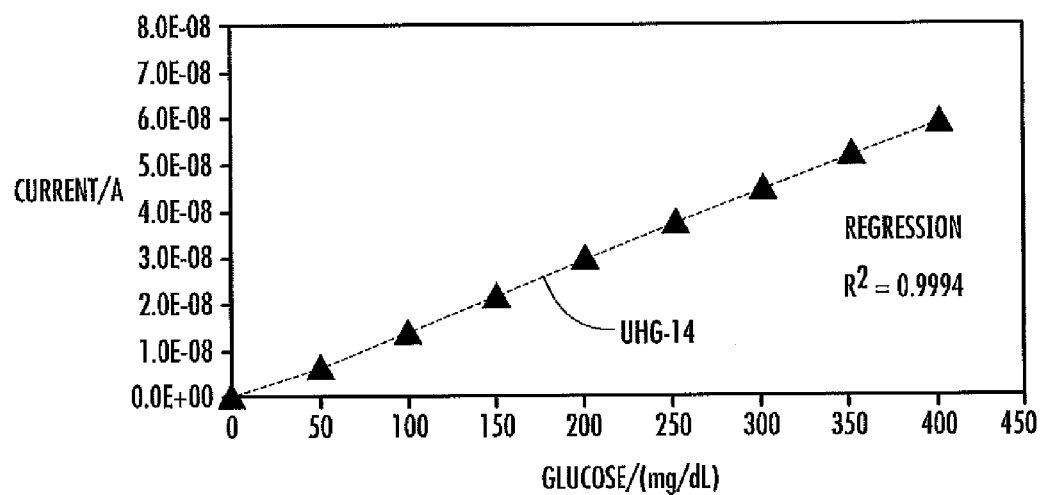
Figure 21:
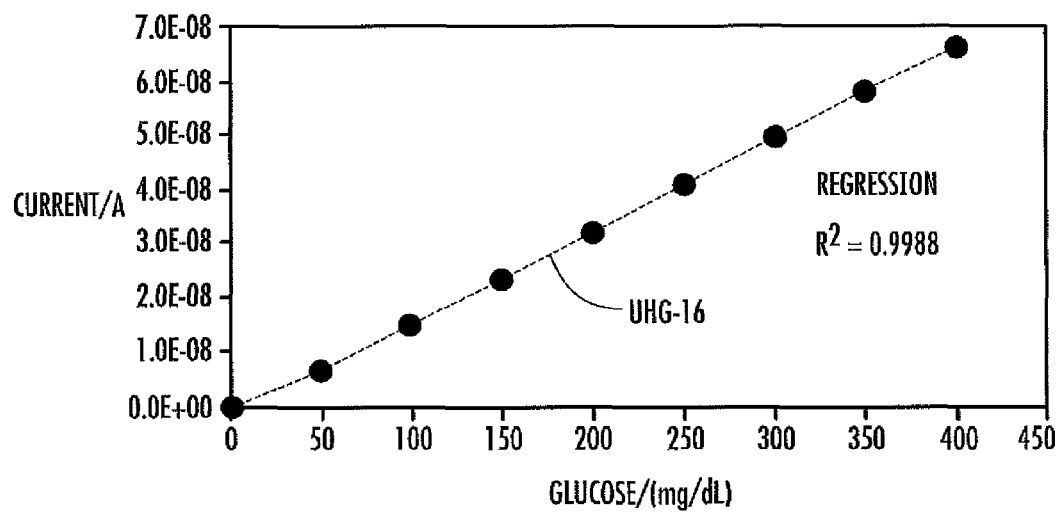

FIG. 12 depicts drift stability provided by the sodium carbonate/PBS buffering system for the collection of sensors (UHD-08, 10, 11, and 12) of FIG. 7. Thus, current output verses time of sensors contacted with high glucose concentrations for extended periods of time using 20 mM sodium carbonate/PBS buffering system at 37° C. maintained linearity without significant drift of signal. The x-axis represents time, the y-axis represents current. The sensors were connected to a potentiostat using a working electrode potential of about 850 mV for 10 minutes before adjusting the voltage to the working potential of about 650 mV .vs. Ag/AgCl prior to testing. As shown, the sensors contacted with the 20 mM bicarbonate/PBS buffering system at a pH of about 7.4 at 37° C., containing high concentration of glucose (400 mg/dL or more) maintained linearity beyond 8 hrs, with a signal drift less than about 10%, where the "drift" was calculated by the % change in sensor output signal between one specified time point and another specified time point while the sensor is continually exposed to a non-changing environment containing a constant analyte concentration. Experiments conducted at 100 mM bicarbonate/PBS buffering system produced similar results.

FIGS. 13-17 are graphical representations showing current output verses time of glucose sensors and the corresponding calibration curves for the individual sensors (UHD-08, 10, 11, and 12) tested under reduced oxygen partial pressure environments (~20 mmTorr/$pO_2$) using a 20 mM sodium carbonate/PBS buffering system. In these graphs, regression lines are dotted and the sensor-derived data points are indicated by geometrical symbols. Thus, the data indicates the bicarbonate-comprising buffering system is useful for determining low oxygen partial pressure performance of test sensors.

FIGS. 18-21 are graphical representations showing calibration curves of the glucose sensors (UHG-02, 03, 14 and 16) based on the data depicted in FIG. 6B. In these graphs, regression lines are dotted and the sensor-derived data points are indicated by geometrical symbols. Thus, the 10×PBS buffering system provided improved performance over the 1×PBS buffering system but slightly less than the buffering system comprising bicarbonate.

It may be seen from the foregoing data (FIGS. 7 & 13) that the linearity of the test sensors are maintained, especially at high glucose concentrations using the bicarbonate-comprising buffering system. As demonstrated, the exemplary sensors had excellent linearity and maintained the linearity over time periods beyond 8 hrs. Thus, a buffering system for electrochemical sensors comprising at least one of acetate ion, carbonate ion, bicarbonate ion, or combinations thereof is useful for in vitro, electrochemical analyte sensor testing, validation, and/or QC-related protocols.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification may be to be understood as being modified in all instances by the term "about." Accordingly, unless indicated to the contrary, the numerical parameters set forth herein may be approximations that may vary depending upon the desired properties sought to be obtained. At the very least, each numerical parameter should be construed in light of the number of significant digits and ordinary rounding approaches.

The above description discloses several methods and materials. These descriptions are susceptible to modifications in the methods and materials, as well as alterations in the fabrication methods and equipment. Such modifications will become apparent to those skilled in the art from a consideration of this disclosure or practice of the disclosure. Consequently, it is not intended that this disclosure be limited to the specific embodiments disclosed herein, but that it cover all modifications and alternatives coming within the true scope and spirit of the claims.

What is claimed is:

1. An electrochemical analyte sensor comprising:
   at least one electrode having an electroactive surface;
   an analyte sensing membrane, at least a portion of the membrane covering the electroactive surface, the membrane comprising:
   an optional interference layer;
   an enzyme layer;
   an optional hydrophilic polymer layer positioned (i) between the electroactive surface and the optional interference layer and/or (ii) between the optional interference layer and the enzyme layer; and
   at least one buffering agent associated with the analyte sensing membrane, wherein the buffering agent comprises a polycation salt, the polycation salt comprising at least one of acetate ion, carbonate ion, bicarbonate ion, or combinations thereof.

2. The sensor of claim 1, wherein the buffering agent is (i) a dried layer between the electroactive surface and the optional interference layer; (ii) a dried layer between the optional interference layer and the enzyme layer; (iii) associated with the optional hydrophilic polymer layer, the optional hydrophilic layer positioned (a) between the electroactive surface and the optional interference layer and/or (b) between the optional interference layer and the enzyme layer; or (iv) any or combinations of (i)-(iii).

3. The sensor of claim 1, wherein the buffering agent provides a signal drift at 400 mg/dL, glucose or more of 10% or less over a time period up to 8 hours or more.

4. The sensor of claim 1, wherein the at least one buffering agent is present in an amount sufficient to neutralize at least one of an acidic, electrochemically produced by-product of the enzyme layer over the clinical concentration range of analyte.

5. The sensor of claim 1, wherein the interference layer is cellulose acetate butyrate.

6. The sensor of claim 1, wherein the enzyme layer comprises an enzyme and a material selected from the group consisting of poly-N-vinylpyrrolidone, poly-N-vinyl-3-ethyl-2-pyrrolidone, poly-N-vinyl-4,5-dimethyl-2-pyrrolidone, polyvinylimidazole, poly-N-N-dimethylacrylamide, polyacrylamide, polyurethanes, and copolymers thereof.

7. The sensor of claim 1, wherein the optional hydrophilic polymer is poly-N-vinylpyrrolidone.

8. The sensor of claim 1, wherein the optional hydrophilic polymer excludes an enzyme.

9. The sensor of claim 1, further comprising a flux-limiting membrane, wherein the flux-limiting layer is a sealant or encapsulant of the analyte sensing membrane.

10. The sensor of claim 1, wherein the flux-limiting membrane is selected from the group consisting of vinyl polymers, polysilicones, polyurethanes, and copolymers or blends thereof.

11. The sensor of claim 1, wherein the flux-limiting membrane is poly(ethylene-vinylacetate).

12. An electrochemical analyte sensor comprising:
at least one working electrode having an electroactive surface;
an analyte sensing membrane comprising:
a hydrophilic layer;
an optional interference layer;
an enzyme layer; and
at least one buffering agent consisting of a polycation salt of any one of acetate ion, carbonate ion, bicarbonate ion, or mixtures thereof, the at least one buffering agent being: (i) a dried layer between the electroactive surface and the optional interference layer; (ii) a dried layer between the optional interference layer and the enzyme layer; (iii) associated with the optional hydrophilic polymer layer, the hydrophilic layer positioned (a) between the electrode surface and the optional interference layer and/or (b) between the optional interference layer and the enzyme layer; (iv) associated with the enzyme layer; or (v) any or all combinations of (i)-(iv);
wherein the hydrophilic layer is positioned (i) between the electroactive surface and the optional interference layer or enzyme layer and/or (ii) between the optional interference layer and an enzyme layer, the hydrophilic layer comprising at least one hydrophilic polymer and excluding an enzyme.

13. The sensor of claim 12, wherein the at least one buffering agent is present in an amount sufficient to neutralize at least one of an acidic, electrochemically produced by-product of the enzyme layer over the clinical concentration range of analyte.

14. The sensor of claim 12, wherein the enzyme layer comprises an enzyme and a material selected from the group consisting of poly-N-vinylpyrrolidone, poly-N-vinyl-3-ethyl-2-pyrrolidone, poly-N-vinyl-4,5-dimethyl-2-pyrrolidone, polyvinylimidazole, poly-N-N-dimethylacrylamide, polyacrylamide, polyurethane, and copolymers thereof.

15. The sensor of claim 12, wherein the hydrophilic polymer is poly-N-vinylpyrrolidone.

16. The sensor of claim 12, further comprising a flux-limiting membrane covering the enzyme layer, the optional interference layer, the hydrophilic layer, and the at least one electrode wherein the flux-limiting membrane is selected from the group consisting of vinyl polymers, polysilicones, polyurethanes, and copolymers or blends thereof.

17. The sensor of claim 16, wherein the flux-limiting membrane is poly(ethylene-vinylacetate).

18. The sensor of claim 12, wherein the sensor is constructed on a flex circuit, wherein the flex circuit comprises at least one reference electrode and at least one working electrode, and at least one counter electrode, the flex circuit being (i) configurable to a catheter for intravenously measuring an analyte concentration in a subject; and/or (ii) configurable to a continuous blood glucose monitor for continuously measuring the glucose concentration in a subject.

19. An in vitro, electrochemical analyte sensor testing method, the method comprising:
providing an electrochemical sensor;
contacting the electrochemical sensor to an aqueous solution comprising a buffering agent, wherein the buffering agent comprises acetate ion, carbonate ion, bicarbonate ion, phosphate buffered saline (PBS) of at least 0.030 molality $Na_2HPO_4$ and at least 0.006 molality $KH_2PO_4$, or any combination of acetate ion, carbonate ion, bicarbonate ion, and phosphate buffered saline (PBS), the buffering agent providing a signal drift at 400 mg/dL glucose or more of 10% or less over a time period of at least one hour;
contacting the electrochemical sensor with one or more concentrations of analyte, the one or more concentrations of analyte being in the clinical concentration range of the analyte; and
testing the electrochemical analyte sensor.

20. The method of claim 19, wherein the buffering agent is present in an amount sufficient to:
(i) neutralize acidic, electrochemically generated by-products of the electrochemical analyte sensor over the clinical concentration range of the analyte in vitro; and/or
(ii) provide essentially a constant output current at the upper end of the clinical concentration range of the analyte for at least two hours when tested in vitro.

21. The method of claim 20, wherein the buffering agent comprises phosphate buffered saline (PBS) buffer, wherein the total molar amount of carbonate ion, bicarbonate ion, or mixture of carbonate and bicarbonate ions is at least 20 mM.

22. The method of claim 19, wherein the buffering agent provides a signal drift at 400 mg/dL glucose or more of 10% or less over a time period up to 8 hours or more.

* * * * *